(12) United States Patent
Greenberg et al.

(10) Patent No.: US 8,647,287 B2
(45) Date of Patent: Feb. 11, 2014

(54) WIRELESS SYNCHRONIZED MOVEMENT MONITORING APPARATUS AND SYSTEM

(76) Inventors: Andrew Greenberg, Portland, OR (US); Pedro Mateo Riobo Aboy, Portland, OR (US); James McNames, Portland, OR (US); Sean Pearson, Beaverton, OR (US); Gavin Gallino, Portland, OR (US); Timothy Brandon, Beaverton, OR (US)

( * ) Notice: Subject to any disclaimer, the term of this patent is extended or adjusted under 35 U.S.C. 154(b) by 0 days.

(21) Appl. No.: 13/037,310

(22) Filed: Feb. 28, 2011

(65) Prior Publication Data
US 2011/0214030 A1 Sep. 1, 2011

Related U.S. Application Data

(63) Continuation-in-part of application No. 12/632,778, filed on Dec. 7, 2009.

(60) Provisional application No. 61/308,764, filed on Feb. 26, 2010, provisional application No. 61/120,485, filed on Dec. 7, 2008.

(51) Int. Cl.
*A61B 5/103* (2006.01)

(52) U.S. Cl.
USPC .......................................... 600/595; 702/141

(58) Field of Classification Search
USPC .......................................... 600/595; 702/141
See application file for complete search history.

(56) References Cited

U.S. PATENT DOCUMENTS

| | | | | |
|---|---|---|---|---|
| 4,117,834 A | * | 10/1978 | McPartland et al. | 600/595 |
| 4,306,291 A | * | 12/1981 | Zilm et al. | 600/552 |
| 4,353,375 A | * | 10/1982 | Colburn et al. | 600/595 |
| 5,293,879 A | * | 3/1994 | Vonk et al. | 600/595 |
| 5,562,104 A | * | 10/1996 | Hochberg et al. | 600/595 |
| 7,089,148 B1 | * | 8/2006 | Bachmann et al. | 702/151 |
| 7,141,026 B2 | * | 11/2006 | Aminian et al. | 600/595 |
| 7,210,240 B2 | * | 5/2007 | Townsend et al. | 33/512 |
| 7,395,181 B2 | * | 7/2008 | Foxlin | 702/155 |
| D614,979 S | * | 5/2010 | McNames et al. | D10/65 |
| 2002/0109621 A1 | * | 8/2002 | Khair et al. | 341/174 |
| 2004/0015103 A1 | * | 1/2004 | Aminian et al. | 600/595 |
| 2005/0010139 A1 | * | 1/2005 | Aminian et al. | 600/595 |

(Continued)

FOREIGN PATENT DOCUMENTS

| | | | | |
|---|---|---|---|---|
| DE | 4117834 A1 | * | 12/1992 | C21C 5/00 |
| DE | 4306291 A1 | * | 9/1994 | G01G 17/00 |

OTHER PUBLICATIONS

Maroti et al., "The Flooding Time Synchronization Protocol", "SenSys '04: Proceedings of the 2nd international conference on Embedded networked sensor systems", Nov. 3-5, 2004 in Baltimore MD, pp. 39-49.*

*Primary Examiner* — Max Hindenburg
*Assistant Examiner* — Renee Danega
(74) *Attorney, Agent, or Firm* — Mateo Aboy; Aboy & Associates PC

(57) ABSTRACT

Disclosed embodiments include a movement monitoring apparatus comprising a wireless synchronization scheme. Depending on the particular embodiment such wireless synchronization scheme is a master synchronization scheme or a mesh synchronization scheme. Additionally, in a particular embodiment, the movement monitor further comprises a robust wireless data transfer data controller. The disclosure includes a description of the complete system, namely, the wireless synchronized movement monitors with robust data transfer capabilities, the docking station, the access point, and the computer-implemented analysis system.

18 Claims, 16 Drawing Sheets

(56) References Cited

U.S. PATENT DOCUMENTS

| | | | |
|---|---|---|---|
| 2005/0234309 A1* | 10/2005 | Klapper | 600/300 |
| 2007/0032748 A1* | 2/2007 | McNeil et al. | 600/595 |
| 2007/0249968 A1* | 10/2007 | Miesel et al. | 600/595 |
| 2007/0255118 A1* | 11/2007 | Miesel et al. | 600/300 |
| 2008/0053253 A1* | 3/2008 | Moore et al. | 73/865.4 |
| 2008/0154098 A1* | 6/2008 | Morris et al. | 600/300 |
| 2008/0284650 A1* | 11/2008 | MacIntosh et al. | 342/357.14 |
| 2008/0285805 A1* | 11/2008 | Luinge et al. | 382/107 |
| 2009/0281830 A1* | 11/2009 | McNames et al. | 705/2 |
| 2010/0030119 A1* | 2/2010 | McNames et al. | 600/595 |
| 2010/0076348 A1* | 3/2010 | McNames et al. | 600/595 |
| 2010/0145236 A1* | 6/2010 | Greenberg et al. | 600/595 |

\* cited by examiner

WIRELESS SYNCHRONIZED MOVEMENT MONITORING APPARATUS AND SYSTEM

CROSS-REFERENCE TO RELATED APPLICATIONS

This application is a Continuation-In-Part of U.S. patent application Ser. No. 12/632,778 filed on 2009 Dec. 7, which claims the benefit of U.S. Provisional Application No. 61/120,485 filed on 2008 Dec. 7, and are hereby incorporated by reference in their entirety. This application also claims the benefit of U.S. Provisional Application No. 61/308,764 filed on 2010 Feb. 26, which is incorporated herein by reference in its entirety.

TECHNICAL FIELD

Disclosed embodiments relate to the physiologic monitoring of movement. Specifically, they relate to systems and devices for continuous and ambulatory measurement of the symptoms of movement disorders using wearable monitoring devices.

BACKGROUND

A. Movement Monitors

State of the art movement disorder monitors employ inertial sensors, such as accelerometers and gyroscopes, to measure position, velocity and acceleration of the subject's limbs and trunk. Current monitors fall into two classes, namely activity monitors and inertial monitors, both of which have disadvantages and limitations that make them incapable of continuous monitoring of movement disorders in ambulatory settings.

Activity monitors, such as in U.S. Pat. No. 4,353,375, collect low frequency and low resolution samples of the subject's gross activity for days to weeks at a time. These monitors are usually small, unobtrusive devices resembling watches or brooches which are worn by the subject for long periods of time such as days or weeks outside of the clinical setting. They measure movement using low quality inertial sensors at low sampling frequencies, and usually measure only a few degrees of freedom of motion instead of all six possible degrees of freedom of motion. The low quality measurements are stored in data storage on-board the device which is later downloaded and analyzed. While they are useful for recording the gross activity levels of the subject, and they may be comfortable and unobtrusive enough to be worn by the subject for longs periods of time, they are only useful in measuring non-subtle symptoms of movement disorders such as activity versus rest cycles. Subtle symptoms, such as symptom onset and decline, or non-obvious symptoms such as bradykinesia, can not be measured by these devices. These devices, also known as actigraphers, typically measure movement counts per minute which make even simple determinations such as determining the wake-up time challenging. Consequently, actigraphers are inappropriate for continuous ambulatory monitoring of movement disorders such as in Parkinson's disease.

Inertial monitors, such as in U.S. Pat. No. 5,293,879, collect high frequency, high resolution samples of the subject's movements for short periods of time. These devices are larger and more obtrusive, resembling small boxes which are worn by the subject for short periods of time such as hours, or at most, a day, and usually in clinical settings. They measure movement using high quality inertial sensors, and usually include all six degrees of freedom of motion (three linear axes and three rotational axes). Inertial monitors may store the inertial measurements in the device for later analysis, or they may use telemetry radios to wirelessly transmit the measurements in real-time to a nearby computer or recording device. These devices are useful for measuring all symptoms of movement disorders, but because of their larger, obtrusive size and short operational times, they are not useful for measuring symptoms outside of clinical settings or for long periods of time.

Movement disorder monitoring can be enhanced by monitoring multiple locations on a subject at the same time. Current systems either do not synchronize their measurements, or require wires to synchronize sampling. Additionally, current movement disorder monitoring devices also lack aiding sensors, such as absolute measures of position.

Movement monitoring devices and systems that overcome challenges of physical size, power consumption, and wireless synchronization are currently unavailable and have significant potential in numerous applications including clinical practice and research.

Currently, the most common and accurate method of tracking movement is based on optical motion analysis systems. However, these systems are expensive, can only measure movements in a restricted laboratory space, and cannot be used to observe patients at home.

Current inertial monitoring systems can be divided into three categories: computer-tethered, unit-tethered, and untethered. Computer-tethered devices connect the sensor directly to a computer. One of the best systems in this category is MotionNode (GLI Interactive LLC, Seattle). These systems are not practical for home settings. Unit-tethered systems connect the sensors to a central recording unit that is typically worn around the waist. This unit typically houses the memory, batteries, and wireless communications circuits. Currently, these systems are the most widely available and are the most common in previous studies. One of the best systems in this category is the Xbus kit (Xsens, Netherlands). This system includes up to five sensors, each with high-performance, triaxial accelerometers, gyroscopes, and magnetometers. The system can operate continuously and wirelessly stream data via Bluetooth to a laptop for over 3 h at distances up to 100 m. However the system is too cumbersome and difficult to use in a home study due to the wires connecting the sensors and central recording unit, the battery life is too short, and the interconnecting wires may be hazardous during normal daily activities. The typical untethered system combines the batteries, memory, and sensors in single stand-alone units. The only wireless untethered systems reported in the literature are "activity monitors," which measure the coarse degree of activity at intervals of 1-60 s, typically with a wrist-worn device that contains a single-axis accelerometer. These devices are sometimes called actigraphs or actometers. Most of these devices only report activity counts, which are a measure of how frequently the acceleration exceeds a threshold. Some custom activity monitors directly compute specific metrics of motor impairment, such as tremor. A few studies have shown that activity monitors worn over 5-10 days could detect on/off fluctuations, decreased activity from hypokinesia, and increased activity associated with dyskinesia. However, typical activity monitors cannot distinguish between motor activity caused by voluntary movement, tremor, or dyskinesia. They do not have sufficient bandwidth, memory, or sensors for precise monitoring of motor impairment in PD. They also cannot distinguish between periods of hypokinesia and naps.

Recently, Cleveland Medical Devices (Cleveland, Ohio) introduced two untethered systems, the KinetiSense and Kinesia devices. These systems include triaxial accelerometers and gyroscopes with bandwidths of 0-15 Hz, but lack magnetometers. Although large, the central recording units could to be worn on the wrist. The sensor and recording unit can be connected to form a single unit. This devices can record data continuously and store it on an on-board memory for up to 12 h. However, 1) the due to their size it is difficult for several of these devices to be used at the same time (e.g. wrist, ankle, waits, trunk), 2) the storage capability is limited to a single day and consequently it is difficult to conduct multiple day studies, and 3) the devices are not synchronized.

Movement monitoring devices and systems that overcome the challenges of 1) physical size (volume), 2) power consumption, 3) wireless synchronization, 4) wireless connectivity, 5) automatic calibration, and 6) noise floor; are currently unavailable and have significant potential in numerous applications including clinical practice and research. Finally, the limited solutions currently available are device-centric and do not include a complete platform to perform collection, monitoring, uploading, analysis, and reporting.

B. Wireless Synchronization

While there are several commercial movement monitors available capable of wireless data transmission, currently none of these movement monitors is capable of providing wireless synchronization of the sampling instances. The most advanced inertial monitors capable of wireless data transfer such as Xsens' full body motion capture monitor (XSens Technologies) require wires between each of the movement monitors and a central unit in order to synchronize the sampling instances of each of the monitors. Synchronization is critical for applications where more than one movement monitor is needed.

Wireless sensor networks have multiple independent nodes all sensing environmental factors at the same time. In the case of a wearable wireless movement monitor, these environmental factors are the kinetic state of the various limbs of a subject wearing two or more movement monitors. Later, during data analysis, the samples of the two or more movement monitors must correlated in time to make any sense together. For example, two movement monitors on the ankles need to be correlated in time in order to show the difference between a lopsided gallop and a smooth run. The problem is that in order to be correlated in time, the sensors must sample at the same time, and, over time, at the same rate, over a long time period of hours, or even days.

There are many ways to do this correlation, but the challenge with small wireless sensor systems is how to go about providing this synchronization of the sampling time and rate without unduly impacting other system parameters.

One way in which current wireless sensor networks synchronize with each other is to provide a wired sync line between nodes. While simple and effective, this not only provides annoying wires running between nodes, but obviously defeats the wireless part of the wireless sensor network.

Another way wireless sensors synchronize their sampling time and rates is by attempting to post-process the data to correlate common events in time. The problem is that disparate sensor locations can sometimes have very little data in common, and many times there is not enough information in common to quickly and reliably correlate the data. For example, a movement monitor on the right wrist and left ankle usually have very little kinetic information in common.

Another way that post processing can be done is by purposely injecting a signal into all sensors at the same time. For movement monitors, this requires the subject to do a sudden, rapid motion at regular intervals, like a jump or a fall. This rapidly becomes annoying to the subject, and produces unreliable synchronization information, especially if the subject does not perform the synchronization move correctly because they're tired—or even asleep.

Another synchronization method for wireless sensor networks is to start the sampling at a known time when the units are together, and then rely on a high precision timing source in each node, such as a temperature compensated crystal oscillator, to keep the units synchronized. This has the disadvantage that such high precision timing sources are usually large and consume much more power—sometimes as much as ten times the power—as regular timing components. Further, despite the significant reduction in the timing drift using high precision timing components, drift is not eliminated, and over long timer periods, like days, these devices do drift. Worse, if the various components experience different temperatures (such as one motion monitor on the sternum under a jacket and one exposed to the elements on a wrist), then the drift is much worse.

C. Robust Wireless Data Transfer

In small, highly mobile wireless devices, such as wireless movement monitors, it is necessary to robustly stream large amounts of data (100 s of bits to 100 s of kilobits per second) in near real time (without large latencies in transmission) over a radio frequency communication channel. These continuous, real-time wireless transmissions often suffer from unpredictable data loss due to a variety of environmental factors, including distance between transmitter and receiver, absorption of the signals by local materials (including human bodies), multipath interference due to objects which reflect or refract signals, and even interference from other devices. The challenge with these small embedded systems is how to go about guaranteeing transmission of the signal without unduly impacting other system parameters.

One way in which current wireless movement monitors overcome transmission problems, such as distance and interference, is to increase the radio frequency (RF) signal strength of their transmissions and/or to use receive amplifiers. Either method leads to an large increase in consumed power, which leads to larger battery sizes, which leads to dramatically larger and heavier devices, forcing some systems to even have large, separate wired unit which holds a replaceable battery pack.

Another way in which current wireless sensors overcome radio problems is by using a high gain antenna. The tradeoff here is that the high gain antenna means large size, so that the antenna size alone can equal the size of the wireless sensor.

A third way these wireless systems overcome radio problems is by using state-of-the-art transmission protocols and encodings. The problem with these systems is that the increased complexity of the radio encoding or protocol requires large RF chipsets and increased power consumption, both of which negatively impact size and weight.

A fourth way to overcome radio transmission issues is by having a local data buffer on-board the sensor, which allows later re-transmission of the data packet when the transmission issue has been solved (that is, the interference is over or the transmission distance has been reduced). The problem here is that small embedded devices usually employ a microcontroller that has small amounts of RAM (usually 10 s to 100 s of kilobytes) which allows buffering of only a few seconds of data before the buffers overflow.

None of these ways to overcome radio communication disruptions allows a wireless sensor to remain small, reduce power consumption, and avoid data loss during long interruptions in communication.

SUMMARY

Disclosed embodiments include a movement monitoring apparatus comprising a wireless synchronization scheme. Depending on the particular embodiment such wireless synchronization scheme is a master synchronization scheme or a mesh synchronization scheme. Additionally, in a particular embodiment, the movement monitor further comprises a robust wireless data transfer data controller.

BRIEF DESCRIPTION OF THE DRAWINGS

Disclosed embodiments are illustrated by way of example, and not by way of limitation, in the figures of the accompanying drawings.

DETAILED DESCRIPTION

A. Overall System Components

Figure 1:
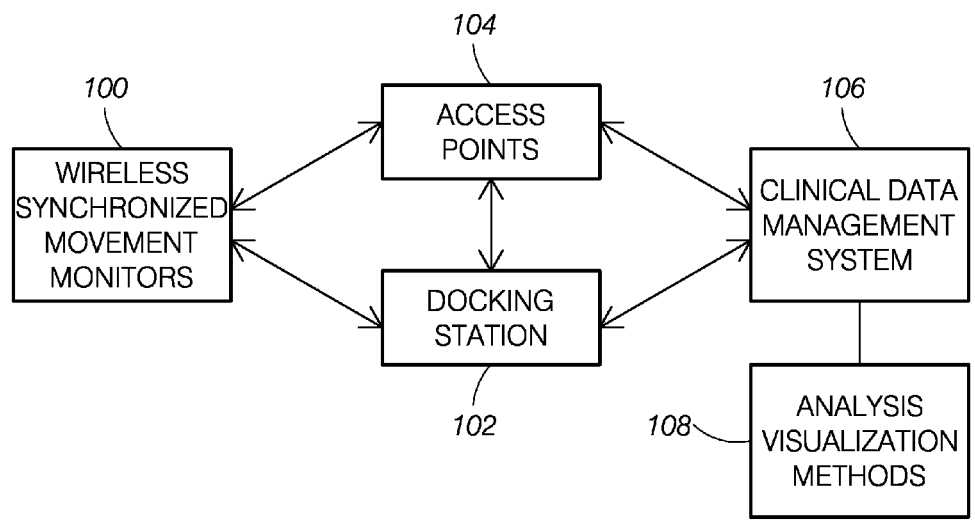
FIG. 1 illustrates a block diagram representing the basic components of an embodiment of the general systems for continuous and objective movement monitoring.
Figure 1:
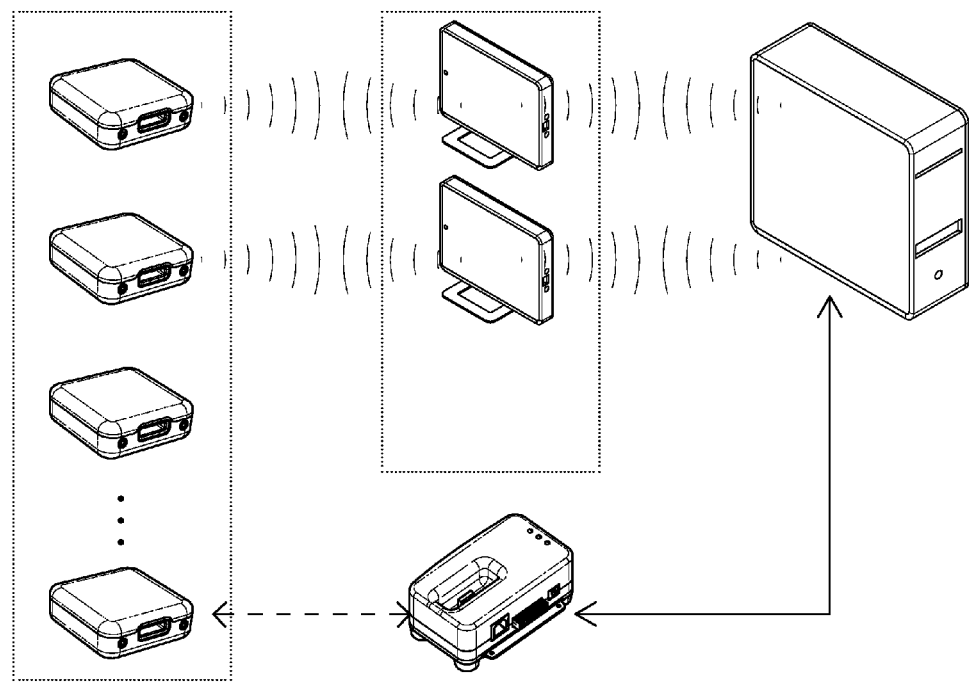
Figure 12:
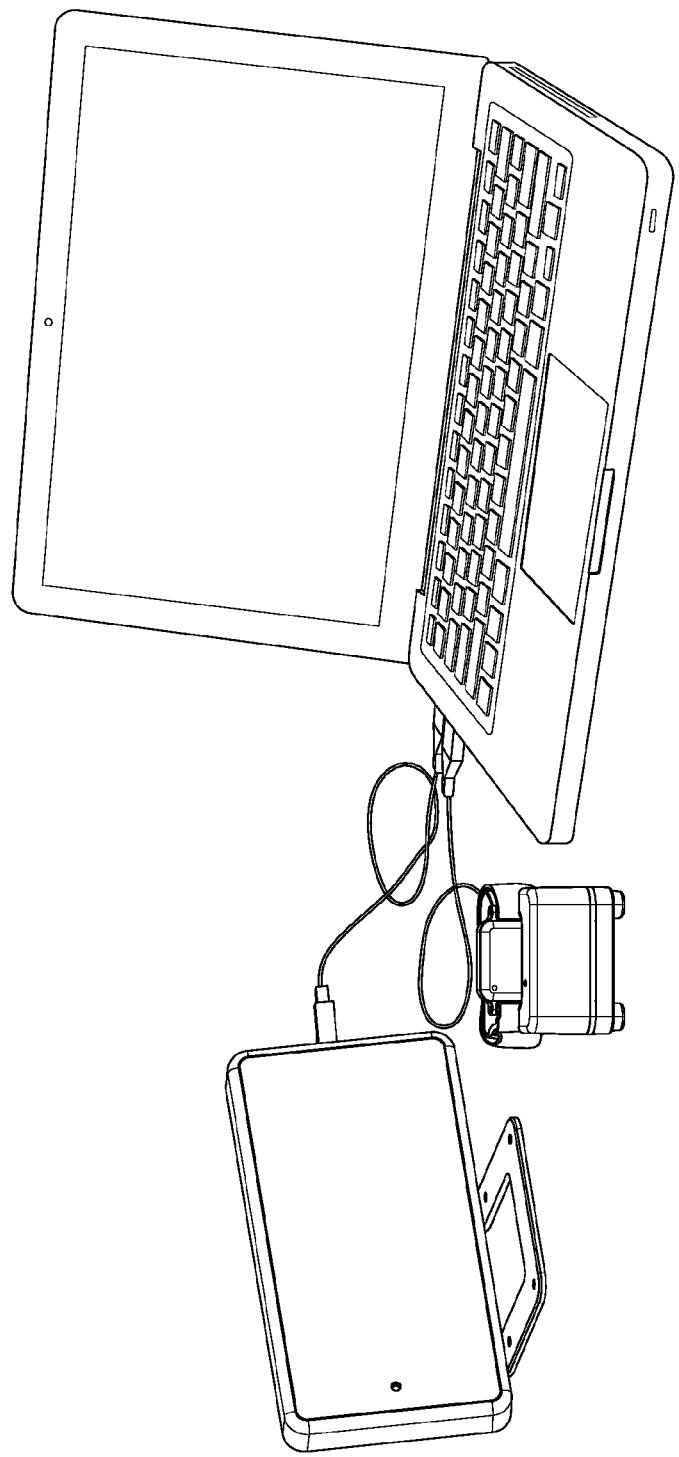
FIG. 12 illustrates a complete system comprise of a movement monitor, a docking station, and access point and a computer system for data analysis and visualization.
Figure 13:
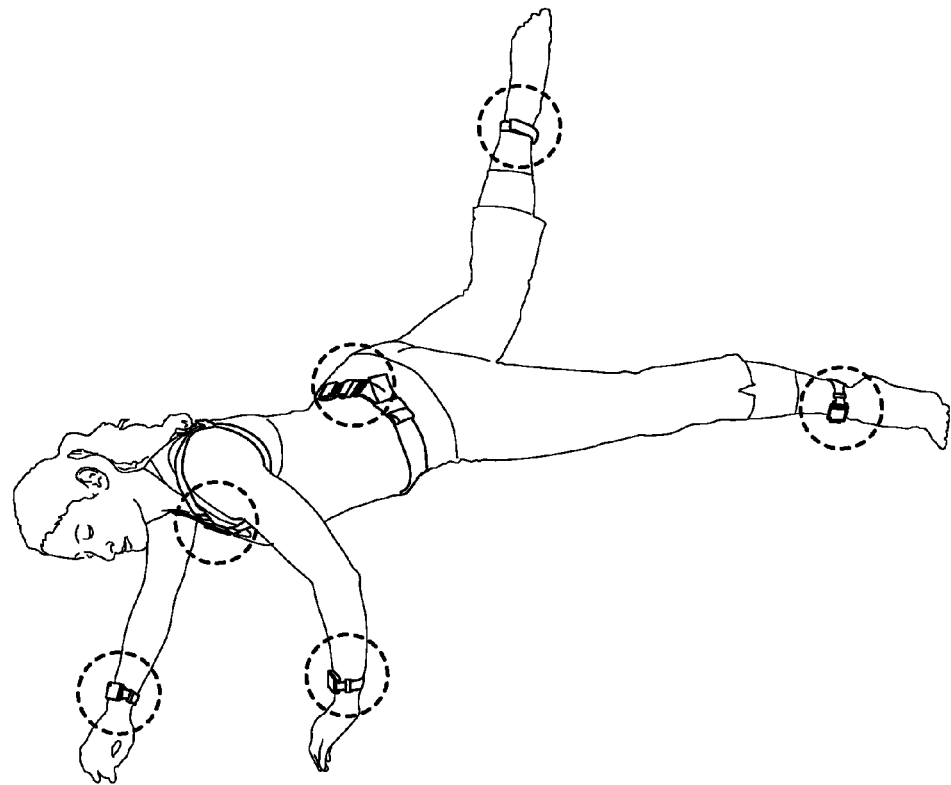
FIG. 13 illustrates an example comparing the use of the disclosed wireless synchronized wearable movement monitors and the closest related prior art.
Figure 13:
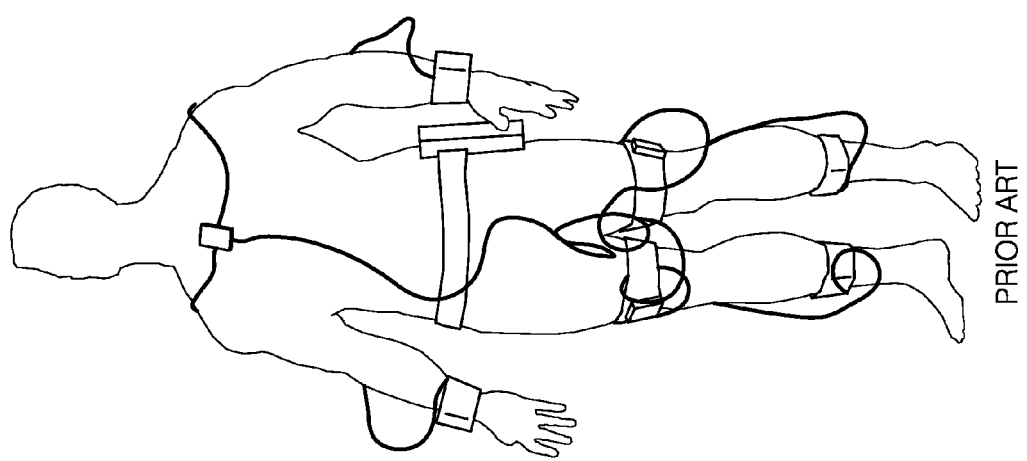
Figure 14:
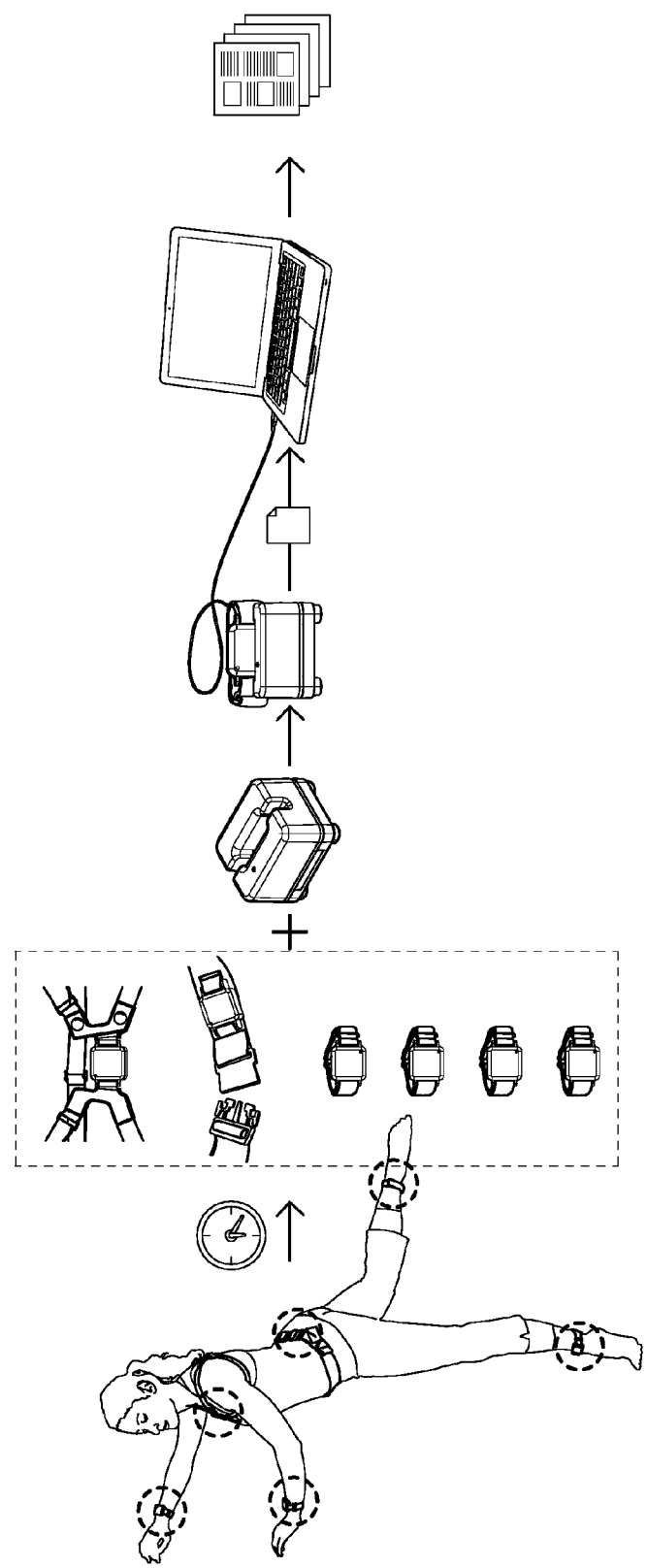
FIG. 14 illustrates the use of the complete system according to one embodiment where wireless mesh synchronized data is collected during continuous ambulatory monitoring by the movement monitors and stored locally until the monitors are docketed and the docking station transfers the data to a computer system including analysis methods to visualize and produce reports of the results.
Figure 15:
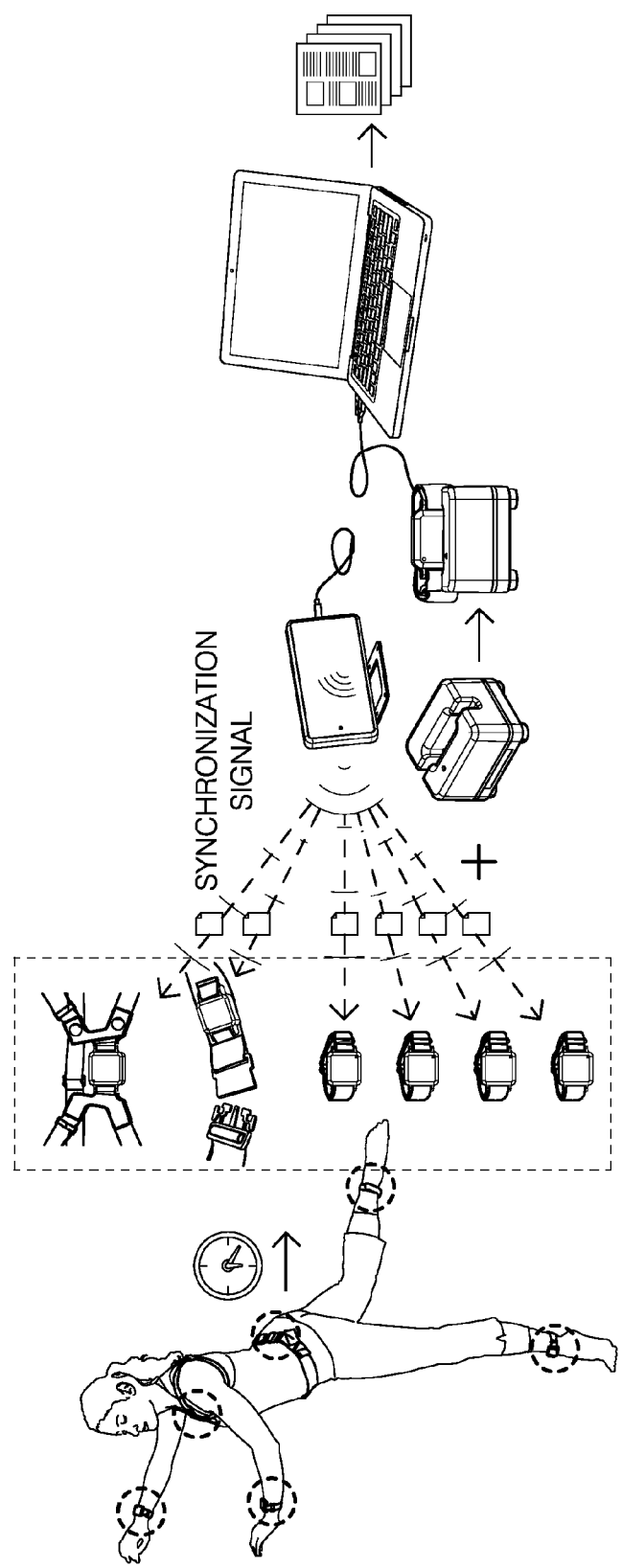
FIG. 15 illustrates the use of the complete system according to one embodiment where wireless master or mesh synchronized data is collected during continuous monitoring by the movement monitors and stored locally until the monitors are docketed and the docking station transfers the data to a computer system including analysis methods to visualize and produce reports of the results.
Figure 16:
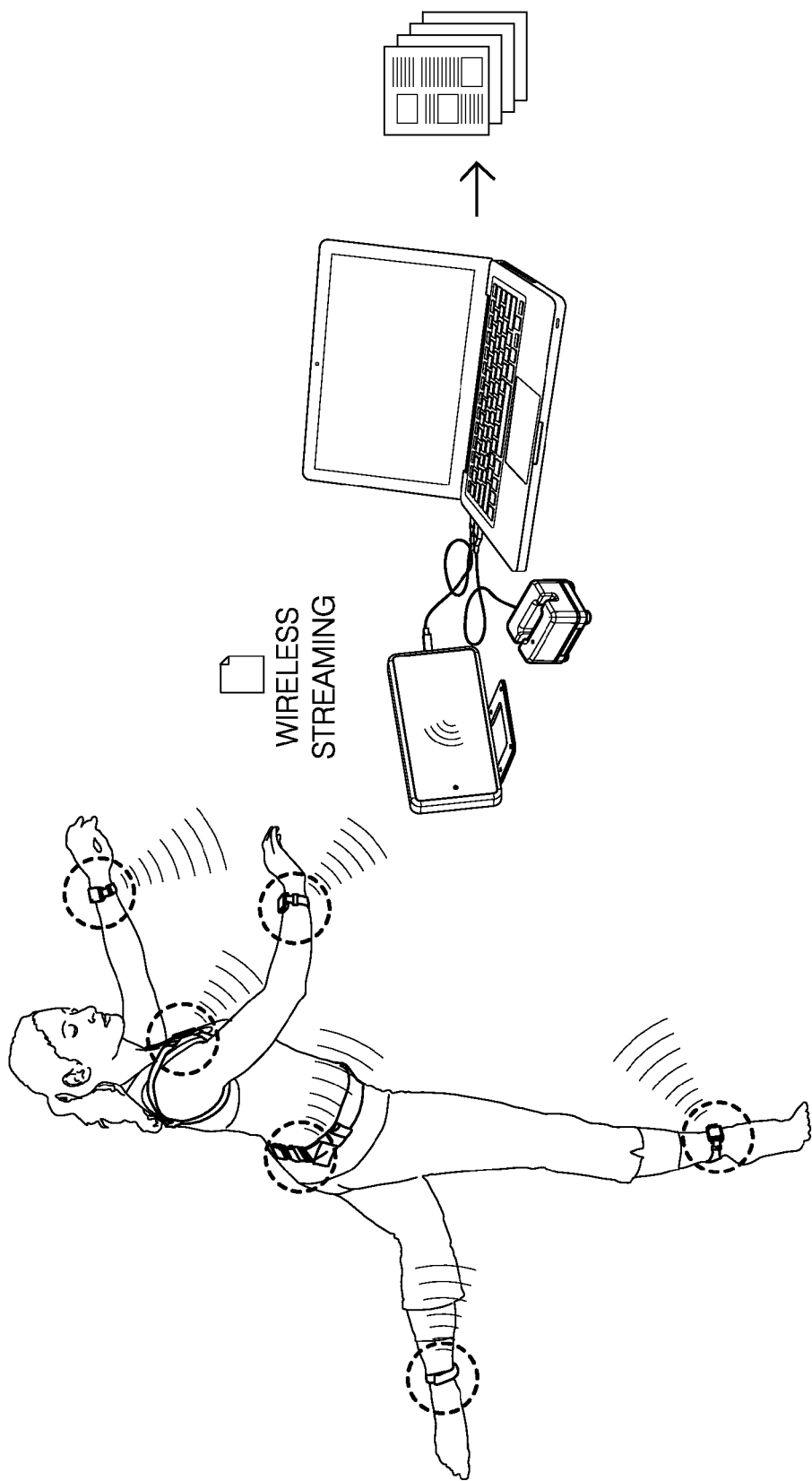
FIG. 16 illustrates the use of the complete system according to one embodiment where wireless mesh synchronized data is collected during continuous or objective monitoring by the movement monitors and such data is wirelessly streamed using robust wireless streaming to a computer system including analysis methods to visualize and produce reports of the results.

According to one embodiment, as shown in FIG. 1 the system for continuous ambulatory monitoring of movement disorders comprises: one or more wearable devices (movement monitors) 100, one or more docking stations 102 connected to a plurality of access points, one or more data servers 104, and a plurality of statistical and signal processing analysis methods 106 to process the movement data collected by the wearable devices and generate a plurality movement metrics. FIG. 12 illustrates a complete system comprise of a movement monitor, a docking station, and access point and a computer system for data analysis and visualization. FIG. 14-16 illustrates several uses of the complete system.

B. Wearable Devices: Movement Monitors

According to one embodiment the wearable movement monitor 100 is a lightweight device (<100 g) comprising (a) a sensor module comprising a plurality of low power (<50 mW) solid state and micro-electromechanical systems kinematics sensors; (b) a microprocessor module comprising a low power (<50 mW) microcontroller configured for device control, device status, and device communication; (c) a data storage module comprising a solid state local storage medium; (d) a wireless communication module comprising a low power (<50 mW) surface mount transceiver and an integrated antenna; and (e) a power and docking module comprising a battery, an energy charging regulator circuit, and a docking connector. In one embodiment, the micro-electromechanical systems kinematics sensors include a plurality of solid-state, surface mount, low power, low noise inertial sensors including a plurality of accelerometers and gyroscopes, as well as a solid-state, surface mount, low power, low noise, Gigantic Magneto-Resistance (GMR) magnetometers. In a particular embodiment, the solid state local storage medium is substantially equivalent to a high capacity SD card (>4 GB) in order to enable for multi-day (>2 days) local storage of movement monitoring data at high frequencies (sampling frequencies>20 Hz). In one embodiment, the communication module is designed to communicate with a plurality of wearable movement monitors (peer-to-peer communication) in order to synchronize the monitors, and to communicate with a host computer (peer-to-host communication) in order to transmit sensor data, uses a bidirectional groundplane PCB patch antenna, and accepts transmissions from a plurality of beacons to calculate the device location. In one embodiment, the power and docking module includes an external connector to access external power and provide high speed communication with an external docking station, the energy charging regulator circuit is a solid state integrated circuit charger such as a linear Lithium Ion Polymer battery charger IC and said battery is a Lithium Ion Polymer battery, and Lithium Ion Polymer battery can be selected for a particular application as a function of its mAHr characteristics (e.g. 450 mAHr or 50 mAHr).

According to another embodiment, the wearable movement monitoring apparatus 100 further comprises an external movement monitoring system comprising: (a) an external docking station for re-charging the wearable movement monitoring apparatus, storing movement data, and transmitting the movement data to a plurality of receiver devices, (b) a plurality of wireless transceiver access points for wireless transmission of the movement data to a plurality of receiver devices, and (c) a web-enabled server computer including a clinical data management and analysis system for storing, sharing, analyzing, and visualizing movement data using a plurality of statistical signal processing methods.

According to an embodiment the movement monitor apparatus 100 is a lightweight, low-power, low noise, wireless wearable device with the following characteristics: 1) weight of 22 g, 2) sampling frequency of 128 Hz, 3) wireless synchronization, 4) 14 bit resolution, 5) three-axis MEMS accelerometers (user configurable from ±2 g to ±6 g), 6) three-axis MEMS gyroscopes with a ±1500 deg/s range, 7) three-axis magnetometers with a ±6 Gauss range, 7) automatically calibrated, 8) over 16 hours of operation per charge, and 9) over 20 days of onboard storage capacity. According to an embodiment the device, and without limitation, the device 100 includes solid state, low-power, low-noise sensors as follows: accelerometer (0.8 cm/s$^2$/sqr(Hz)), XY gyroscope (0.05 deg/s/sqrt(Hz)), z Gyroscope (0.05 deg/s/sqrt(Hz)), and magnetometer (40 nT/sqrt(Hz)).

According to one embodiment, the wearable devices or apparatus 100 are compact movement monitoring devices that continuously record data from embedded sensors. The sensors 100 may be worn at any convenient location on the body that can monitor impaired movement. Convenient locations include the wrists, ankles, trunk, and waist. In one embodiment, the sensors include one or more channels of electromyography, accelerometers, gyroscopes, magnetometers, and other MEMS sensors that can be used to monitor movement. The wearable sensors 100 have sufficient memory and battery life to continuously record inertial data throughout the day from the moment subjects wake up until they go to sleep at night, typically 18 hours or more. In one particular embodiment designed for continuous monitoring of movement during daily activities the device uses a storage element substantially equivalent to an SD card to store movement data for extended periods of time (e.g. 1 month). The sensors 100 automatically start recording when they are removed from the docking station. In one embodiment, there is no need for the user to turn them on or off.

Figure 2:
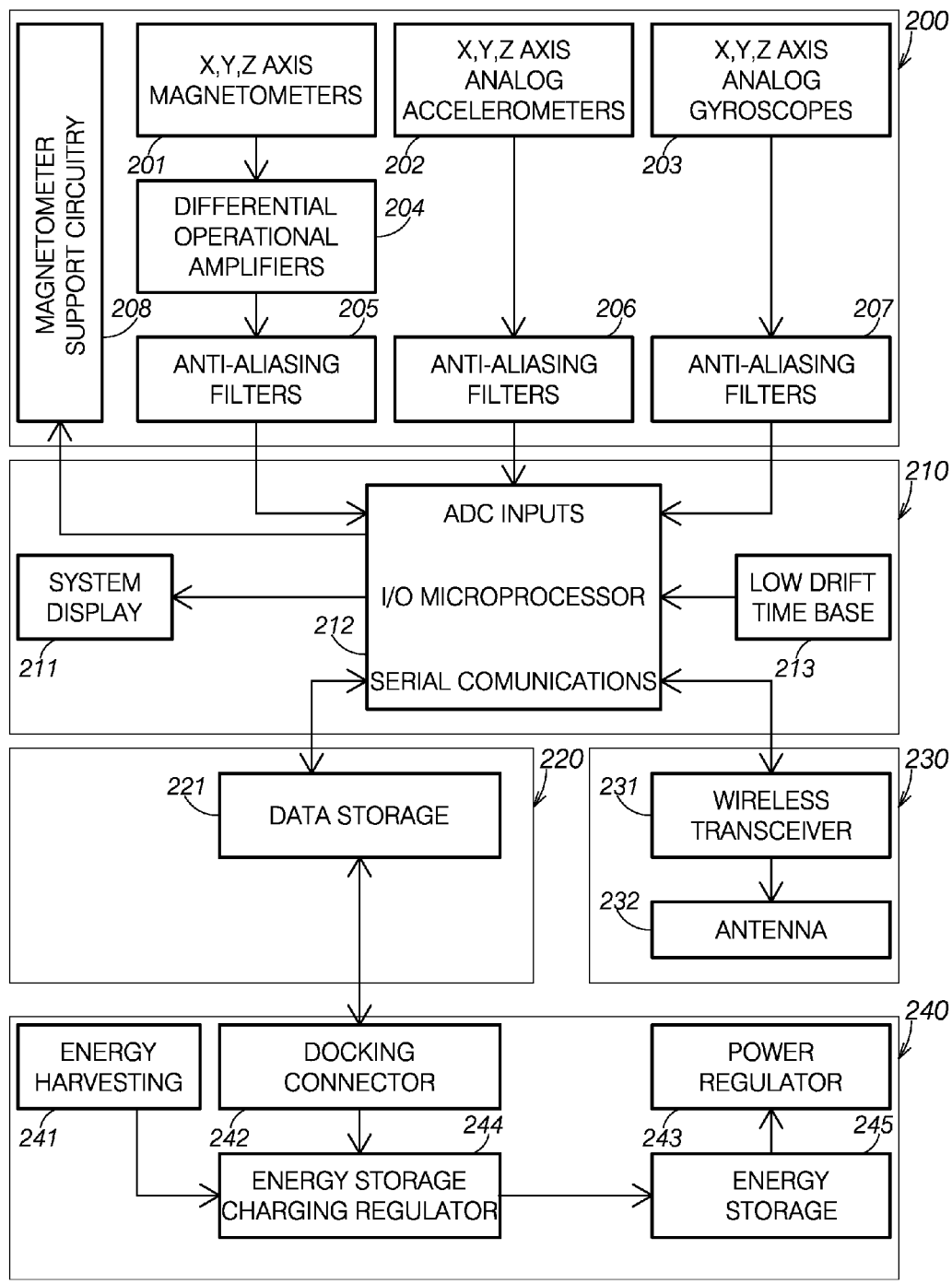
FIG. 2 illustrates a detailed diagram of the basic components and interconnections of an embodiment of the wearable apparatus for continuous and objective movement monitoring.

According to one embodiment, the wearable devices 100 include the components and interconnections detailed in FIG. 2: a sensor module 200, a microprocessor module 210, a data storage module 221, a wireless communication module 230, and a power and docking module 243. An embodiment of each of these modules comprising the apparatus for continuous and objective monitoring of movement disorders is described in detail below. In addition to movement monitoring in clinical applications such as movement disorders, the embodiments disclosed can be use to characterize movement in a plurality of application areas including continuous movement monitoring, activity monitoring, biomechanics, sports science, motion research, human movement analysis, orientation tracking, animation, virtual reality, ergonomics, and inertial guidance for navigation, robots and unmanned vehicles.

Figure 8:
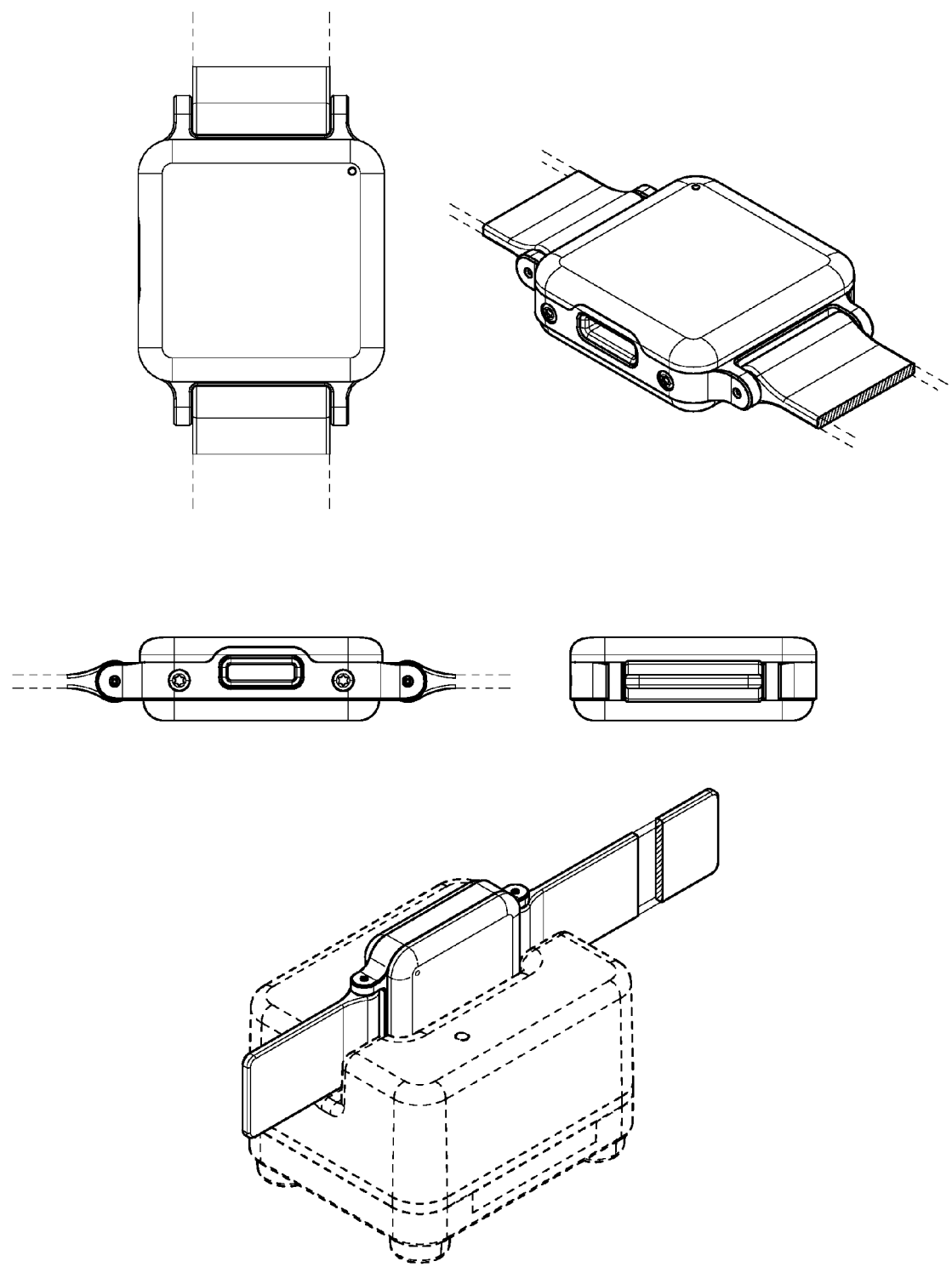
FIG. 8 illustrates a second embodiment of the movement monitor, the docking station, and the docking mechanism, this embodiment particularly adapted to the wearable a wrist watch.
Figure 9:
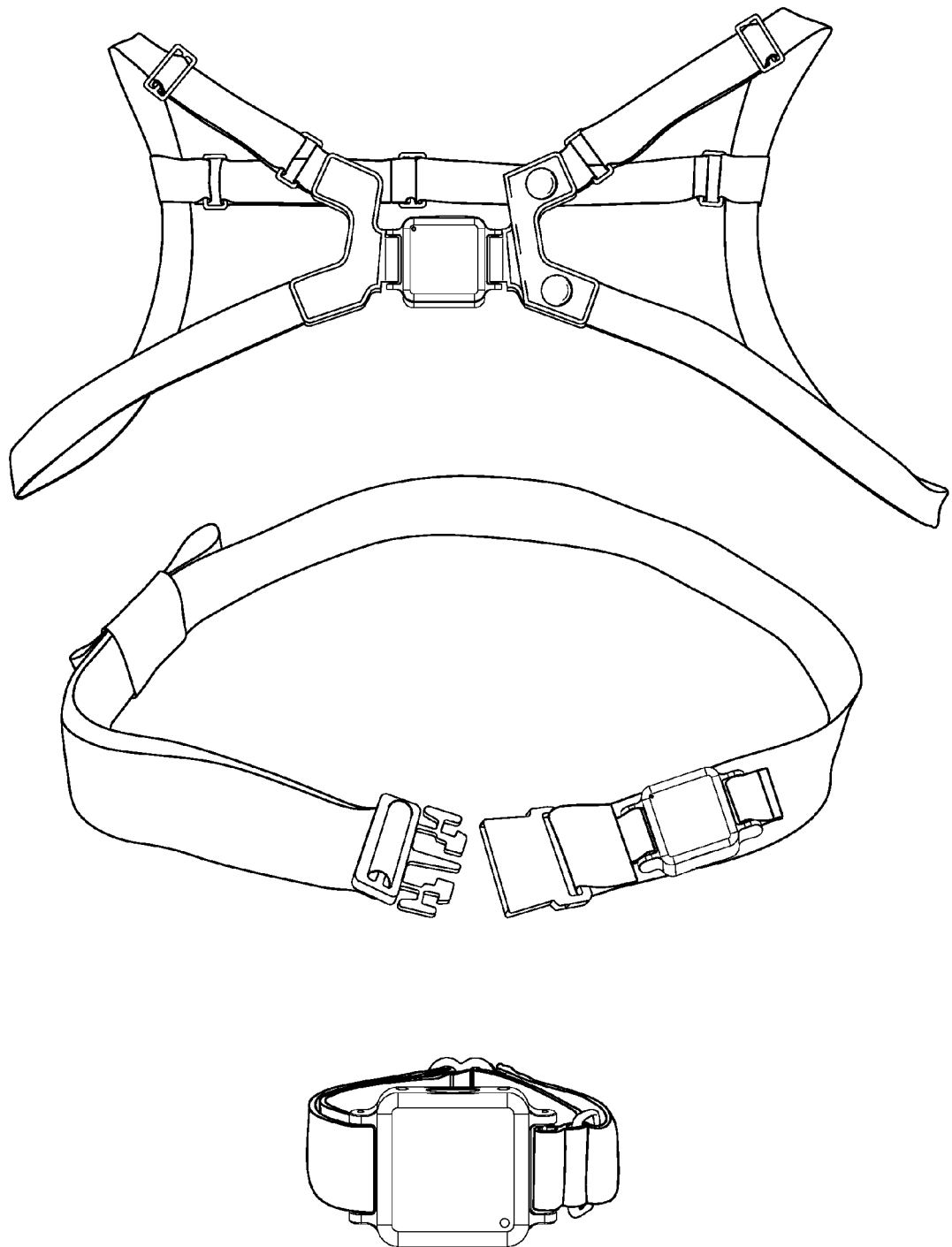
FIG. 9 illustrates embodiments of the movement monitor with sternum, waist, and wrist/ankle straps.

FIG. 8 illustrates a second embodiment of the movement monitor, the docking station, and the docking mechanism, this embodiment particularly adapted to the wearable a wrist watch. FIG. 9 illustrates embodiments of the movement monitor with sternum, waist, and wrist/ankle straps.

B.1. Sensor Module

The sensor module 200 in FIG. 2 contains the motion sensors necessary to characterize the symptoms of movement disorders. Three of these sensors are low noise accelerometers 202. According to one embodiment, the accelerometers are off-the-shelf, commercially available Micro-ElectroMechanical Systems (MEMS) acceleration sensors in small surface-mount packages, such as the STMicro LIS344AHL. In other embodiments, the acceleration sensors are custom made MEMS accelerometers. The accelerometers are arranged in three orthogonal axes either on a single multi-axis device, or by using one or more separate sensors in different mounting configurations. According to one embodiment, the output of the accelerometers 202 is an analog signal. This analog signal needs to be filtered to remove high frequency components by anti-aliasing filters 206, and then sampled by the analog-to-digital (ADC) peripheral inputs of the microprocessor 212. According to one embodiment the anti-aliasing filters are single pole RC low-pass filters that require a high sampling frequency; in another, they are operational amplifiers with multiple-pole low pass filters that may use a slower sampling frequency. In other embodiments, the device includes an analog interface circuit (AIC) with a programmable anti-aliasing filter. According to another embodiment, the output of the accelerometers is digital, in which case the sensor must be configured for the correct gain and bandwidth and sampled at the appropriate rate to by the microprocessor 212.

The next three sensors in the sensor module 200 are solid state, low noise rate gyroscopes 203. In one embodiment, the gryroscopes are off-the-shelf, commercially available Micro-ElectroMechanical Systems (MEMS) rotational sensors in small surface-mount packages, such as a the Invensense IDG-650 and the Epson Toyocomm XV-3500CBY. In other embodiments they are custom made MEMS. The gyroscopes are arranged in three orthogonal axes either on a single multi-axis device, or by using one or more separate sensors in different mounting configurations. According to one embodiment, the output of the gyroscopes 203 is an analog signal. This analog signal needs to be filtered to remove high frequency components by anti-aliasing filters 207, and then sampled by the analog-to-digital (ADC) peripheral inputs of the microprocessor 212. According to one embodiment the anti-aliasing filters are single pole RC low-pass filters that require a high sampling frequency; in another, they are operational amplifiers with multiple-pole low pass filters that may use a slower sampling frequency. In other embodiments, the device includes an analog interface circuit (AIC) with a programmable anti-aliasing filter. According to another embodiment, the output of the gyroscopes is digital, in which case the sensor must be configured for the correct gain and bandwidth and sampled at the appropriate rate to by the microprocessor 212.

The sensor module 200 also contains one or more aiding sensors. According to one embodiment, an aiding system is a three axis magnetometer 201. By sensing the local magnetic field, the magnetometer is able to record the device's two axes of absolute attitude relative to the local magnetic field which can aid correcting drift in other inertial sensors such as the gyroscopes 203. In one embodiment, the magnetometer sensors are off-the-shelf, low noise, solid-state, GMR magnetometer in small surface-mount packages such as the Honeywell HMC1043. In other embodiments they are custom made MEMS. The magnetometers are arranged in three orthogonal axes either on a single multi-axis device, or by using one or more separate sensors in different mounting configurations. According to one embodiment, the output of each magnetometer 203 is an analog signal from two GMR magnetometers arranged in a Wheatstone bridge configuration, which requires a differential operational amplifier 204 to amplify the signal and an anti-aliasing filter 207 to remove high frequency components. These amplified, anti-aliased filters are then sampled by the analog-to-digital (ADC) peripheral inputs of the microprocessor 212. According to one embodiment the anti-aliasing filters are single pole RC low-pass filters that require a high sampling frequency; in another, they are operational amplifiers with multiple-pole low pass filters that may have a slower sampling frequency. In other embodiments, the device includes an analog interface circuit (AIC) with a programmable anti-aliasing filter. According to another embodiment, the output of the magnetometers is digital, in which case the sensor must be configured for the correct gain and bandwidth and sampled at the appropriate rate to by the microprocessor 212. Unlike conventional MEMS inertial sensors, magnetometer sensors may need considerable support circuitry 208, which in one embodiment include such functions as temperature compensation of the Wheatstone bridge through controlling the bridge current, and low frequency magnetic domain toggling to identify offsets through the use of pulsed set/reset coils.

Although not specifically depicted in the sensor module 200, other aiding sensors could be added. In one embodiment, a Global Positioning System Satellite Receiver is added in order to give absolute geodetic position of the device. In another embodiment, a barometric altimeter is added to give an absolute indication of the vertical altitude of the device. In another embodiment, beacons consisting of devices using the same wireless transceiver 231 could also tag specific locations by recording the ID of the beacon.

B.2. Microprocessor Module

The microprocessor module 210 in FIG. 2 is responsible for device control, device status, as well as local data and communication processing. The microprocessor 212 may indicate the device's status on some kind of visual or auditory display 211 on the device. In one embodiment, the display is a a red-green-blue (RGB) light emitting diode (LED). In another embodiment, a small LCD panel is used to display information, such as the time of day, system status such as battery charge level and data storage level, and a medication reminder for subjects who require medication for to treat their movement disorder. In another embodiment, the medication reminder is a gentle vibration, auditory, or visual cue that reminds subjects to take any necessary treatment or perform symptom measurement tasks.

According to one embodiment, the microprocessor 212 is a low power microcontroller such as the Texas Instruments MSP430FG4618. The microprocessor coordinates the sampling of sensors, data processing, data storage, communications, and synchronization across multiple devices. The microprocessor should be a lower power device with enough computational resources (e.g. 20 MIPS) and input/output resources (more than 20 general purpose input/output lines, 12 analog-to-digital converter inputs, and more than two serial communication ports) to interface to other modules.

The microprocessor is clocked by a low drift time base 213 in order to accurately maintain both a real time clock (RTC) and to minimize drift in the synchronous sampling across multiple devices on one subject over long periods of time. In one embodiment, the low drift time base is a temperature compensated crystal oscillator (CTXO) such as the Epson TG3530SA. In another embodiment, the time base is a standard microprocessor crystal with custom temperature compensation using the digital-to-analog converter of the microprocessor 212. Using a CTXO instead of a standard microprocessor crystal also minimizes power consumed by the wireless communication module 230 since the frequency necessary to re-synchronize devices is reduced.

B.3. Data Storage Module

The data storage module 221 stores the measurements from the sensors 200 and status of the device (such as the energy storage device's 245 charge level) locally on the device. It is especially designed to support studies involving multi-day continuous movement monitoring. In one embodiment, the device is capable of storing movement data at a sampling frequency of 128 Hz for over 20 days. In one embodiment, the local storage is flash memory soldered to the device's printed circuit board. In another embodiment, a high capacity Flash card, such as a >4 GB MicroSD card, is used with a high speed synchronous serial port (SPI) from the microprocessor 212 to minimize wire complexity and to enable a standard protocol to hand off to a host computer as necessary. In another embodiment, the data storage module is greatly reduced, or even unnecessary, because data is streamed directly off the device using the wireless communication module 230.

B.4. Wireless Communication Module

The wireless communication module 230 allows the device to communicate to other devices (peer-to-peer), to a host computer (peer-to-host) and to listen to other data such as wireless beacons. The wireless communication module serves multiple functions: it broadcasts data from the device's inertial sensors 200 to a computer or other recording device, it synchronizes sampling rate across multiple devices through a sampling time synchronization protocol, and allows for configuring the devices behavior (i.e. mode of operation). Another use for the wireless communication module is to listen for transmissions from beacons which informs the device about its current location (e.g. bathroom, kitchen, car, workplace). In one embodiment, the communication protocol is a industry standard protocol such as Bluetooth, ZigBEE, WiFi or substantially equivalent protocol. In another embodiment, it is a custom communication protocol based on a physical layer transceiver chip.

One embodiment of the wireless communication module consists of a low power, 2.4 GHz surface mount wireless transceiver 231, such as the Nordic Semiconductor nRF24L01+. The wireless transceiver uses a small on-board antenna 232, such as a chip antenna like the gigaNOVA Mica antenna for both transmitting and receiving wireless communications. In another embodiment, the antenna is a groundplane PCB patch antenna. In one embodiment, the wireless transceiver 231 uses a high speed synchronous serial port, such as the serial peripheral interface (SPI), to communicate with the host microprocessor 212. In another embodiment, the wireless transceiver is built into the microprocessor as a peripheral. In another embodiment, the wireless transceiver uses skin conduction to create a Personal Area Network (PAN) instead of a broadcast radio. Another embodiment uses light, such as infrared light, as a wireless communication system like the industry standard IRDA. In this last embodiment, the antenna 232 would be an optical transceiver.

B.5. Wireless Synchronization

B.5.A. Master Synchronization Scheme

Figure 3:
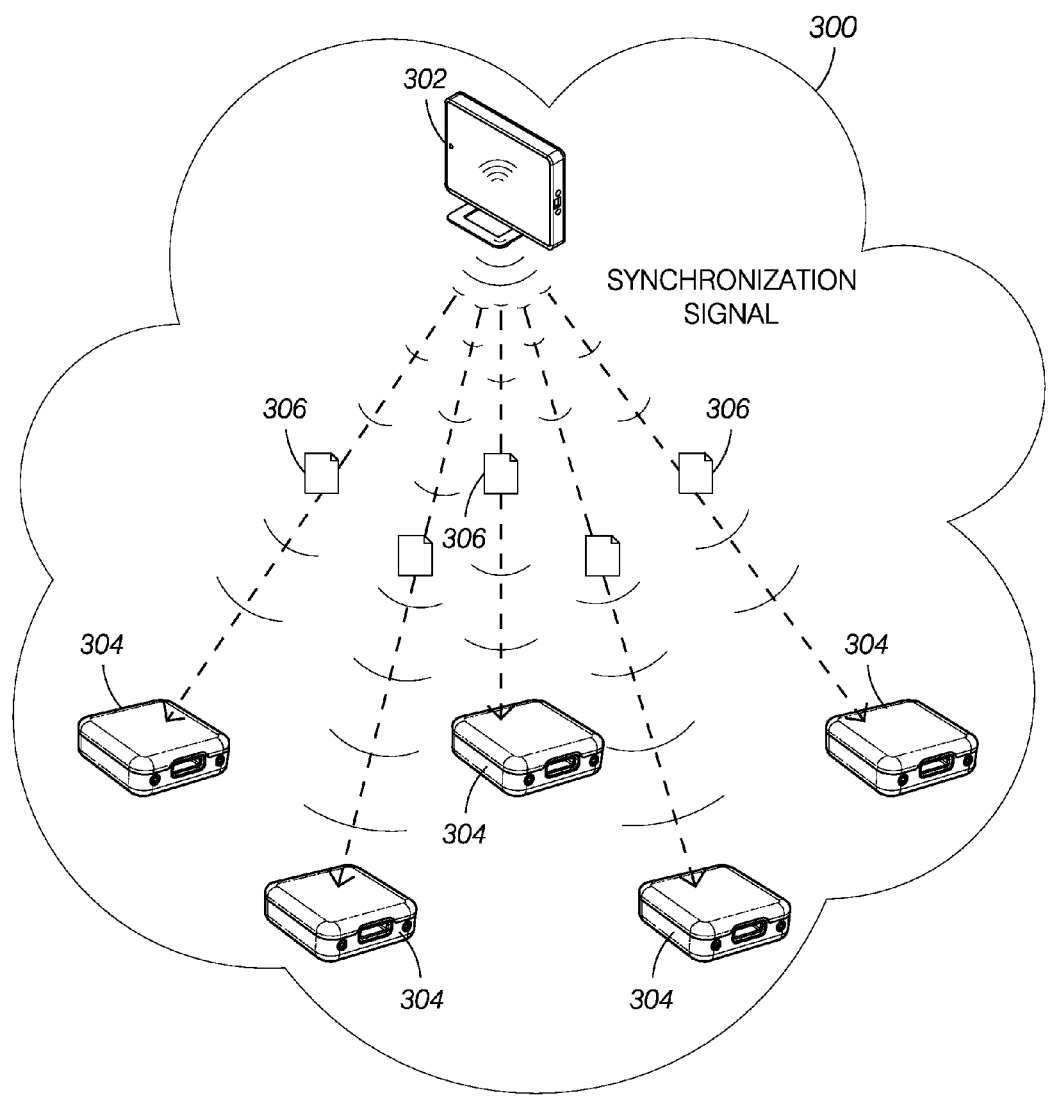
FIG. 3 illustrates a block diagram representing an embodiment of a wireless synchronization scheme based on a single master clock.

According to one embodiment the movement monitor incorporates a wireless synchronization scheme based on master synchronization. In the master wireless synchronization scheme a plurality of movement monitors on a wireless network with a plurality of access points receive the data generated by the wireless network. One of these access points, which is identified during configuration, becomes the master timing source for the entire network. All other access points are synchronized to the master. FIG. 3 illustrates a block diagram representing an embodiment of a wireless synchronization scheme based on a single master clock.

In one embodiment, the access points are synchronized to the master using a cable to transmit a synchronization clock. In another embodiment, the between-access point synchronization signal is sent over the wireless network between access points, possibly on a different wireless channel. In another embodiment, the synchronization signal is sent from the master access point to the other access points via connection to a local host computer.

The access point synchronization signal is used to precisely time the transmission of a synchronization data packet. This data packet is transmitted at the exact same time by all access points and is received by all wireless nodes. This synchronized packet, in one embodiment, contains the counter value representing the time since the epoch for the master access point clock.

On receipt of the synchronization data packet, the wireless nodes adjust their clock or primary timer based on their local time stamp of the reception of that packet. In one embodiment, the nodes utilize a timer-based hardware capture (capture and compare) input pin to get a precise offset between the arrival of the synchronization packet and the device's local time. This offset can be used to measure the drift in the sensor node's clock and allow the node to either adjust its clock frequency directly via a voltage controlled oscillator, or allow it to periodically adjust a counter/timer to be used for sampling.

According to a particular embodiment, and without limitation, a single access point is chosen to be the master access point, and thus the master clock, for the entire wireless network. At the same time, all access points are updated to the same 64 bit absolute time stamp. This access point generates a precisely and deterministically timed clock signal using its PWM peripheral which is distributed to all other access points. On receipt of the clock pulse, each access point enters a high priority interrupt which has a known, deterministic delay to execution. Then each access point executes a predetermined number of instructions to send a synchronization packet from the access points to the rest of the wireless sensor nodes. This synch packet includes the absolute time. The radios on the wireless sensor nodes receive the packet and assert an interrupt line. This interrupt line is tied to a capture and compare peripheral pin, which takes a snapshot of the local timer in an interrupt. This snapshot allows the sensor node to reliably and deterministically find out when exactly the packet was sent according to its onboard time base. The sensor node takes this snapshot and compares it to what it should be, given a known synchronization packet rate. The difference is used in a simple software PLL to synchronize the local timer with the master access point clock.

The advantage to the master synchronization scheme is that it allows the sensor nodes to quickly and easily come into synchronization with the network: it requires very little computation to adjust the local clocks on the nodes, and the isochronous rate of the synchronization packets can be adjusted based on the need for synchronization tolerance. The higher the rate, the less time there is for clock drift.

FIG. 15 illustrates the use of the complete system according to one embodiment where wireless master or mesh synchronized data is collected during continuous monitoring by the movement monitors and stored locally until the monitors are docked and the docking station transfers the data to a computer system including analysis methods to visualize and produce reports of the results.

B.5.B. Mesh Synchronization Scheme

Figure 4:
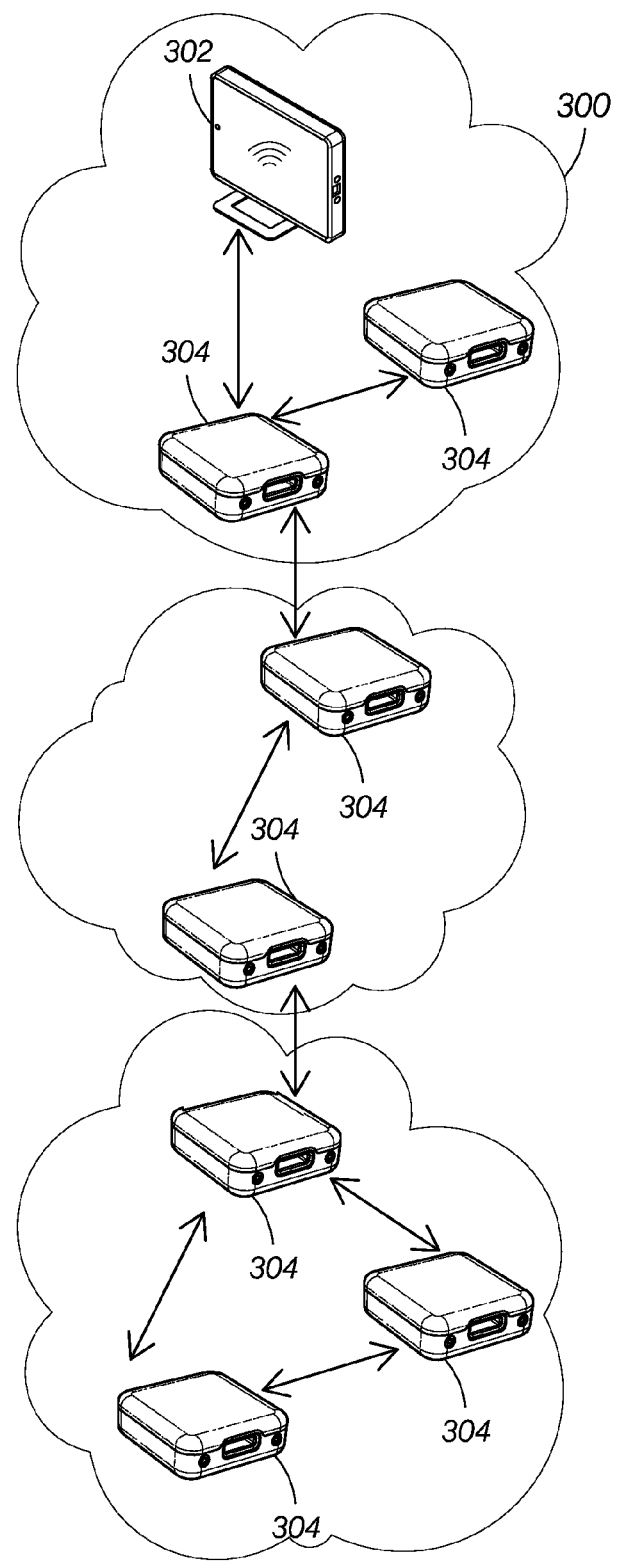
FIG. 4 illustrates a block diagram representing an embodiment of a wireless synchronization scheme based on mesh synchronization.

According to an alternative embodiment the wireless synchronization scheme is comprised of a plurality of sensors on a wireless network with a plurality of access points to receive the data generated by the wireless network. In this scheme, however, there is no master time source. Instead, each device on the network sends a synchronization packet during its prescribed time slot, enabling each device to compare its clock against the clock of each of the other nodes and access points in the wireless network. This comparison allows each node in the mesh to create a statistical model of the network time—a distributed statistical clock model—and of its own clock relative to the network time. FIG. 4 illustrates a block diagram representing an embodiment of a wireless synchronization scheme based on mesh synchronization.

Packet transmission and reception in the mesh synchronization scheme must be deterministic. In one embodiment, the sending and receiving of mesh synchronization packets is tied to a transmit enable from a local hardware timer. The packets will be sent at the exact time according to the local clock, and on receiving the synchronization packets, the nodes will capture their local timer values to determine their relative offsets.

Figure 5:
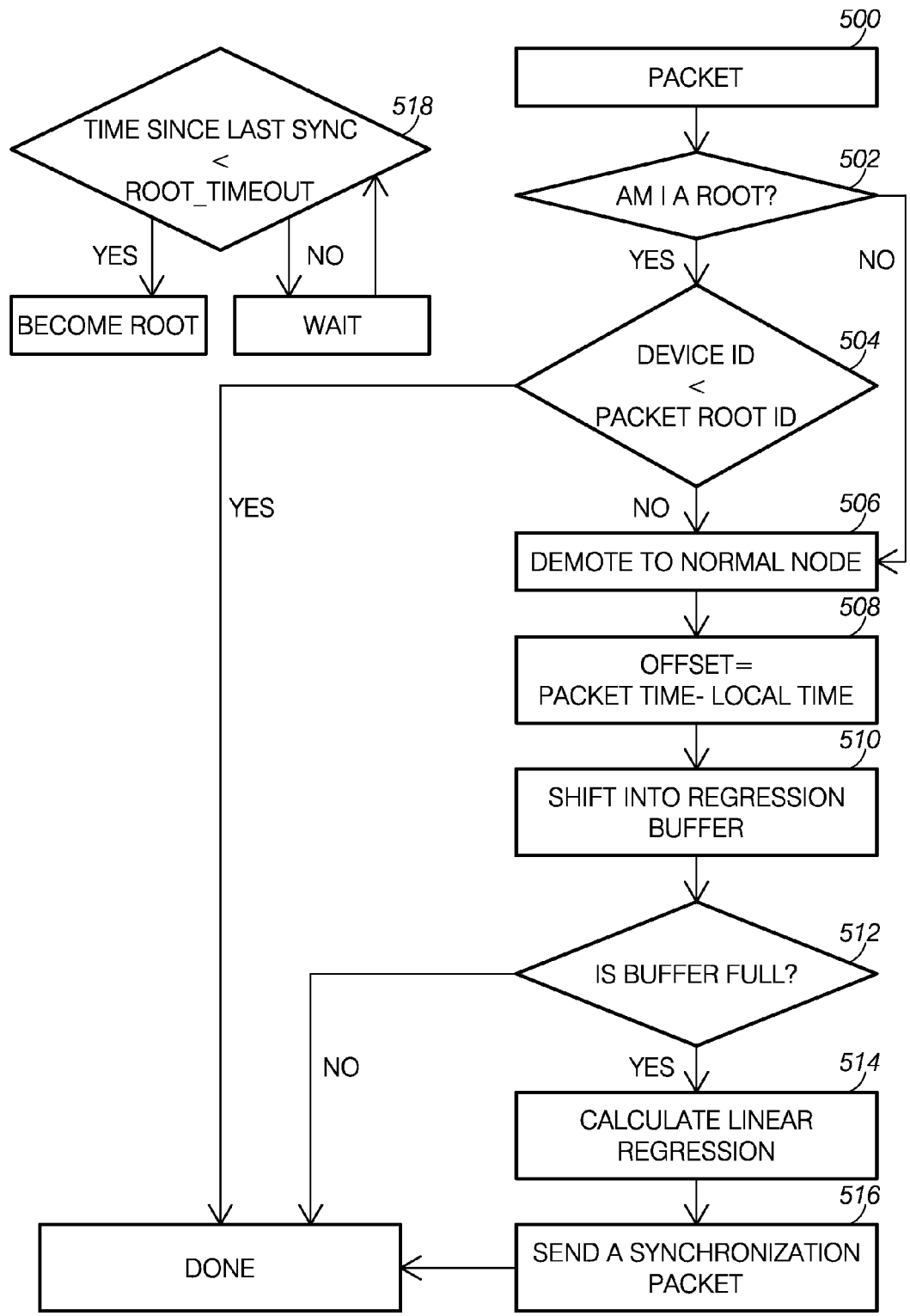
FIG. 5 illustrates a block diagram representing an embodiment of a wireless synchronization scheme based on mesh synchronization using the Flooding Time Synchronization Protocol (FTSP).

In one embodiment, and without limitation, the Flooding Time Synchronization Protocol (FTSP) is used to synchronize the nodes. FIG. 5 illustrates a block diagram representing an embodiment of a wireless synchronization scheme based on mesh synchronization using the Flooding Time Synchronization Protocol (FTSP). A single node is dynamically elected to maintain global time. All other nodes synchronize their clocks to that of this root node. Each node receives synchronization packets from the root node and uses them to build a linear regression model of offset and drift from the global time. Once synchronized, these nodes can broadcast synchronization packets for nodes which are out of range of the root node to use for synchronization. According to one particular embodiment, the FTSP protocol uses two-way messaging to do sender-receiver synchronization propagating out from a root node. The first step in the FTSP mesh synchronization is to dynamically choose a root node. After waiting for the timeout period, ROOT-TIMEOUT, without receiving a synchronization packet each node will declare itself root and start sending out synchronization packets. Upon receiving a synchronization packet from another node, if that node's device ID is lower than a device that has declared itself root, it demotes itself to a normal node. In this way, the node with the lowest device ID will eventually be the only root node. Each time a synchronization packet is received, the node checks to see if it is a root. If it is a root, then it checks to see if its device ID is less than the packet's root ID. If the device ID is less, nothing happens and this node stays a root. If the device ID is greater, this node stops being a root, and uses the packet's root ID for any future synchronization packets it sends out. Whenever a regular node receives a synchronization packet, it calculates the difference between the packet's global time and the local time. This difference is shifted into a buffer for linear regression. If the regression buffer is full, the linear regression is calculated. The linear regression produces an offset and drift estimate. The device is now considered synchronized and can transmit its own synchronization packets with the root ID and the corrected local time whenever it gets a new packet. Each synchronization packet contains the current global time according to the transmitter, the root device ID, and the synchronization packet count. The packet counter is incremented by the root every time a new packet is sent. When a regular node sends a packet it uses the most recent packet count it has received.

In another embodiment, the FTSP is modified such that each synchronized node broadcasts its estimated clock model parameters. The root node can then estimate it's own parameters such that the error of all the clocks from the nominal frequency is minimized. If the distribution of clock frequencies is centered about the nominal frequency, this will reduce drift with respect to actual time. In another embodiment, the Reference Broadcast Protocol is used to synchronize the nodes. A root node is chosen to send synchronization packets. The other nodes then exchange their local times upon receipt of each synchronization packet. In another embodiment, the Timing-sync Protocol for Sensor Networks is used.

In another embodiment, each node in the network will calculate confidence intervals for its own clock and provide this to other nodes for use in calculating the weight that its clock should provide to the statistical network time. In another embodiment, each node calculates the confidence interval for the other nodes based on the variance of received packet time compared to their local clock.

In cases where a node or subset of nodes gets disconnected from the network, they will calculate their own network time using the nodes they can connect to. The larger the network, or the better their local clock, the more confident the unified network time can be. In the case where two or more groups are connected via a small subset of nodes the unified time can be propagated throughout the network. When two or more subsets of the network get completely disconnected from each other the chance for multiple diverging network times can occur. Reconnection of the two subnets is smoothly implemented by using the statistical modeling and allowing only very slow slewing of local clocks.

FIG. 14 illustrates the use of the complete system according to one embodiment where wireless mesh synchronized data is collected during continuous ambulatory monitoring by the movement monitors and stored locally until the monitors are docketed and the docking station transfers the data to a computer system including analysis methods to visualize and produce reports of the results.

B.6. Robust Wireless Data Transfer Controller

Figure 6:
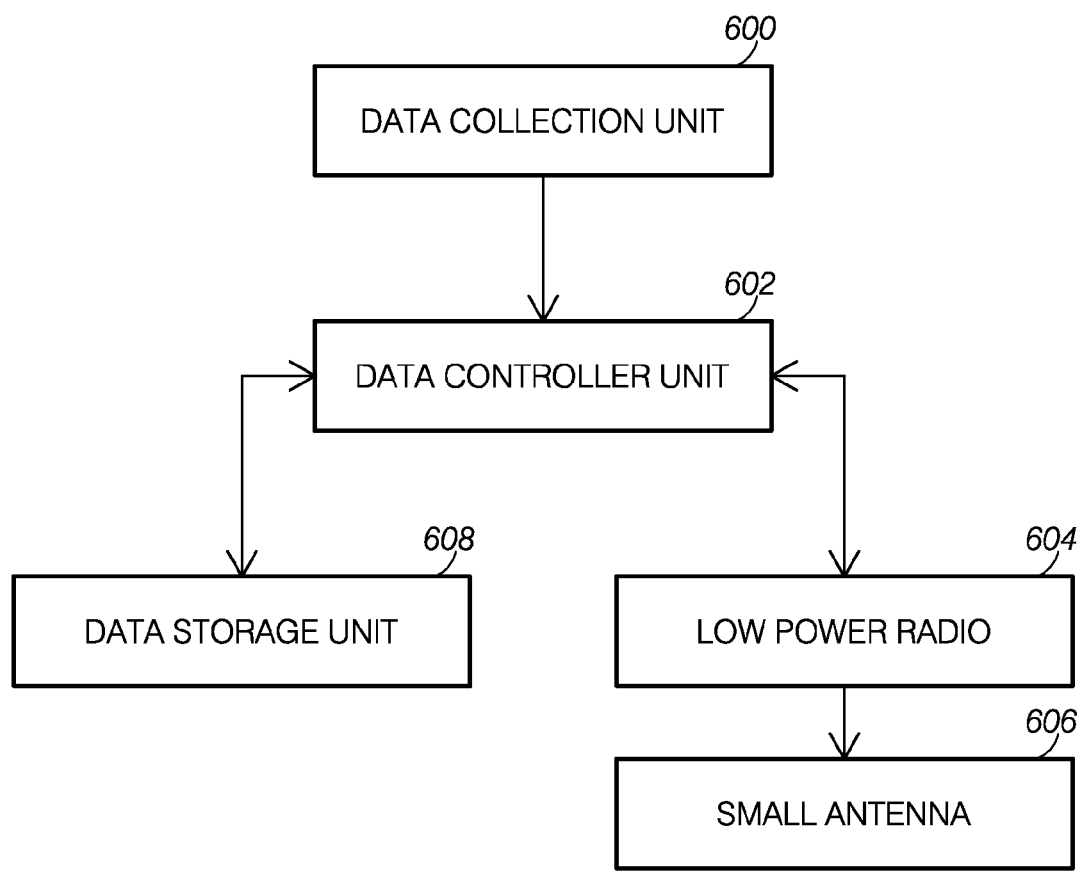
FIG. 6 illustrates a block diagram representing the basic components of an embodiment of for robust wireless communications wireless systems.

FIG. 6 illustrates a block diagram representing the basic components of an embodiment of the general systems for robust wireless communications in small wireless systems including a data collection unit 600, a data controller unit 602, a data storage unit 608, a radio 604, and an antenna 606. Disclosed embodiments include a new apparatus for robust wireless communications for small wireless systems, such as a wearable movement monitor, comprising of (a) a small sized, large capacity, low power, nonvolatile data storage unit, (b) a low power wireless communication system, (c) a small antenna, (d) a data collection unit to collect data to be transmitted, (e) a data controller to control the flow and storage of data in the system, and (f) data controller means to control how the data is processed, stored and transmitted. The data storage unit is a small sized, large capacity, low power, nonvolatile data storage system. In one embodiment, and without limitation, it is a commercially available microSD card with 8 GB of data storage. In another embodiment, it is a large capacity Flash surface-mounted IC. In another embodiment, it is a large capacity SDRAM chip with battery backup.

The low power radio unit is a small volume, extremely low power radio system. In one embodiment, it is a a Nordic Semiconductor nRF24L01+ 2.4 GHz transceiver. In another embodiment, it is a low power IC that conforms to a radio standard such as Bluetooth or IEEE 802.15 (ZigBee). The small antenna is an extremely small volume antenna that trades a reduction in radiation efficiency for an decrease in the occupied volume by the antenna. In one embodiment, the antenna is a small custom made 2.4 GHz PCB patch antenna. In another embodiment, it is a commercially available chip antenna. The data collection unit collects the data to be transmitted. In one embodiment, the data collection unit is a six-degree-of-freedom inertial measurement unit (three axis accelerometers, three axis gyroscopes). In another embodiment, the data collection unit contains a six-degree-of-freedom inertial measurement unit (three axis accelerometers, three axis gyroscopes), a three axis magnetometer, and a temperature sensor. The data controller controls the flow of data from the data collection unit to the data storage unit, and from the data storage unit to the low power radio unit. In one embodiment the data controller is a microcontroller such as the Texas Instruments MSP430FG4618, in another it is a programmable logic device like an FPGA or CPLD.

In order to achieve robust wireless data transfer the system and apparatus includes a data transfer controller 602 that can run one of several methods, optimizing for power, communication bandwidth, or robustness. In one embodiment, the data controller methods running on the data controller store all data from the data collection on the data storage unit, and stream the data from the data storage unit to the low power radio unit as the unreliable radio channel allows.

In another embodiment, the data controller method first sends the data to the lower power radio unit, then stores only the data that has failed to successfully transmit.

In another embodiment, the data controller methods store data in the data storage unit while sensing that the state of the communication channel. If the channel is not available, the data controller methods shuts off the low power radio to save power, and continues to poll the channel until it is available.

In another embodiment, the data controller methods store the data in the data storage unit, and only occasionally turns on the radio into their full speed modes in order to quickly and efficiently "burst" the data from the device.

In another embodiment, the external data storage unit utilizes a single data bus with only half duplex reads and writes. In this case, the data controller methods must schedule and prioritize the data on the data bus. In the case where sensor data is being produced at a constant rate there is a hard real time requirement that writes take precedence over reads to prevent the loss of data. It is therefore possible for the radio unit to be temporarily starved of data pending a read request since a pending read operation is only performed if there are no pending writes in the queue.

In another embodiment, the data controller has a "data latency bound" that enables the data controller methods to keep only so many seconds (or minutes, or hours) of data before discarding the data.

Figure 11:
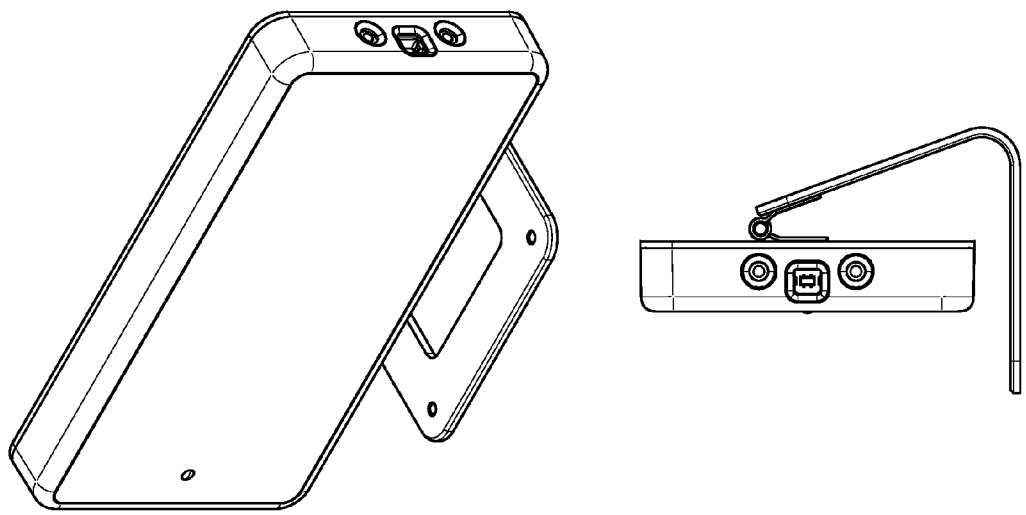
FIG. 11 illustrates an embodiment of the access point.
Figure 11:
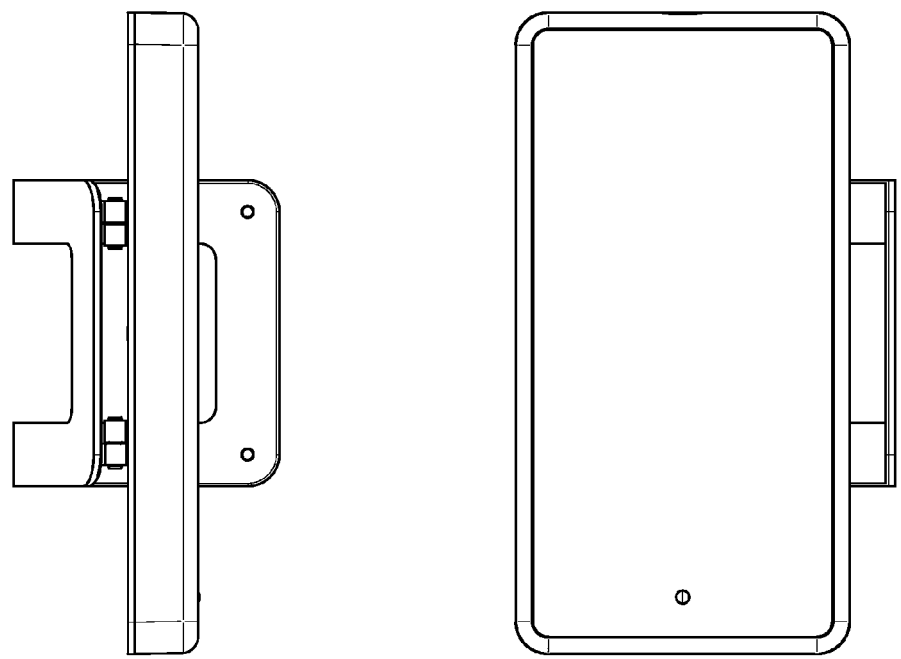

FIG. 11 illustrates an embodiment of the access point. FIG. 16 illustrates the use of the complete system according to one embodiment where wireless mesh synchronized data is collected during continuous or objective monitoring by the movement monitors and such data is wirelessly streamed using robust wireless streaming to a computer system including analysis methods to visualize and produce reports of the results.

B.7. Power and Docking Module

The power and docking module 240 provides external power, power regulation, and external data connections to the device. One aspect of the power and docking module is the docking connector 242 which provides an external connector to access external power and provide high speed communication with the docking station, and thus to a computer or other recording device. One embodiment of the connector 242 is the Hirose ST60 series connector which provides enough connections for both power and complete hand off of the data storage module 220 for extremely high throughput downloading of data. In another embodiment, the docking connector is completely wireless, and provides inductive wireless power transmission for external power and a local high speed wireless data channel.

Most energy storage devices much be carefully charged, so the energy storage charging regulator 244 must carefully charge the energy storage device 245. In one embodiment, the energy storage charger is a linear Lithium Ion Polymer battery charger IC such as the Microchip MCP73833, or substantially equivalent integrated circuit. In another embodiment, it is a switching battery charge IC. In another embodiment, the microprocessor 212 measures the battery capacity and controls the energy storage device's charge directly.

The energy storage mechanism 245 is in one embodiment a Lithium Ion Polymer battery. Other embodiments involve other energy storage mechanism, such as super capacitors or other battery chemistries. The Lithium ion polymer battery should be sized appropriately to be as small as possible for the comfort of the subject wearing the device, yet still contain enough stored energy to power the system for a sufficiently long period of time. In one embodiment, a 450 mAHr battery is used to enable the device to last 24 hours and thus be usable for a full day before recharging is required. In another embodiment, a smaller 50 mAHr battery is used to minimize the device size for short term clinical use.

A power regulator 243 must be used to regulate the power coming from the energy storage device. According to one embodiment, a simple voltage regulator such as the Texas Instruments TPS79901 or equivalent, prepares the energy storage device's power for use by the other modules (200, 210, 210, 220, 230).

Device operation can be extended or performance improved by harvesting energy from the local environment. One embodiment of an energy harvesting device 241 is a small solar panel on the outside of the device. Another is a small kinetic generator using piezoelectric materials to generate voltage. A third uses heat differences between the subject's skin and the ambient air temperature.

B.8. External Docking Station

According to one embodiment, in order to facilitate use in the clinic, home, or other normal daily environments, the device includes a docking station 102 that is used to charge the batteries of the wearable devices 100 and download the data from each day of activities. The docking station 102 uploads the data using whatever means is available in that setting. If high-speed Internet access is available within the home, this may be used for data upload. Alternatively it permits the user to download the data to a portable storage device such as a USB thumb drive or hard drive that can then be transported to a site for final upload to the data server. If there is no simple means to download the data from the docking station 102, the data is downloaded once the docking station is returned at the end of the monitoring period. The docking station 102 requires no user intervention. The devices 100 stop recording as soon as they are docked and start recording as soon as they are undocked. According to one embodiment, the docking station 102 does not include any buttons. The docking station 102 can be connected to a computer for data extraction and processing.

Figure 7:
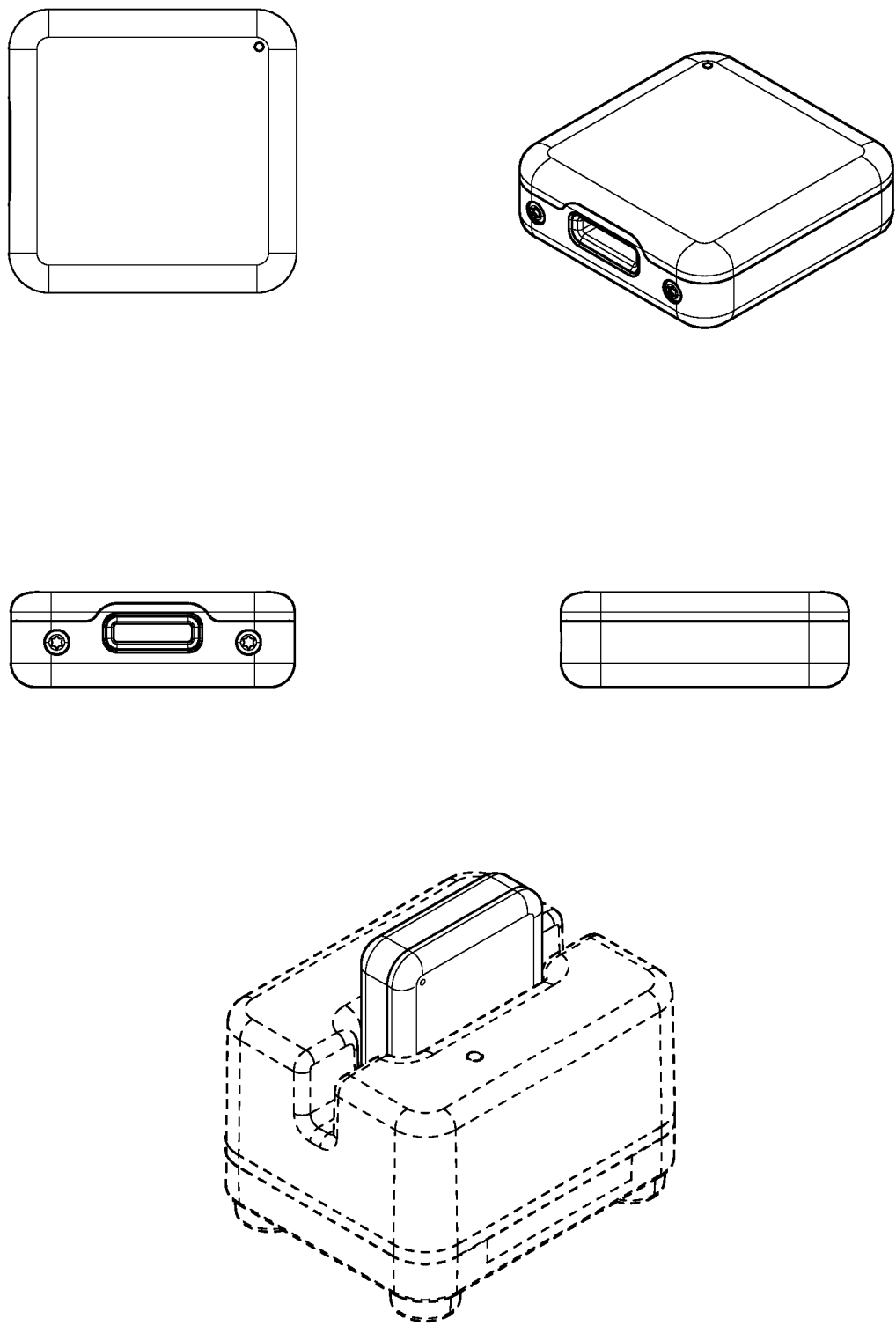
FIG. 7 illustrates a particular embodiment of the movement monitor, the docking station, and the docking mechanism.
Figure 10:
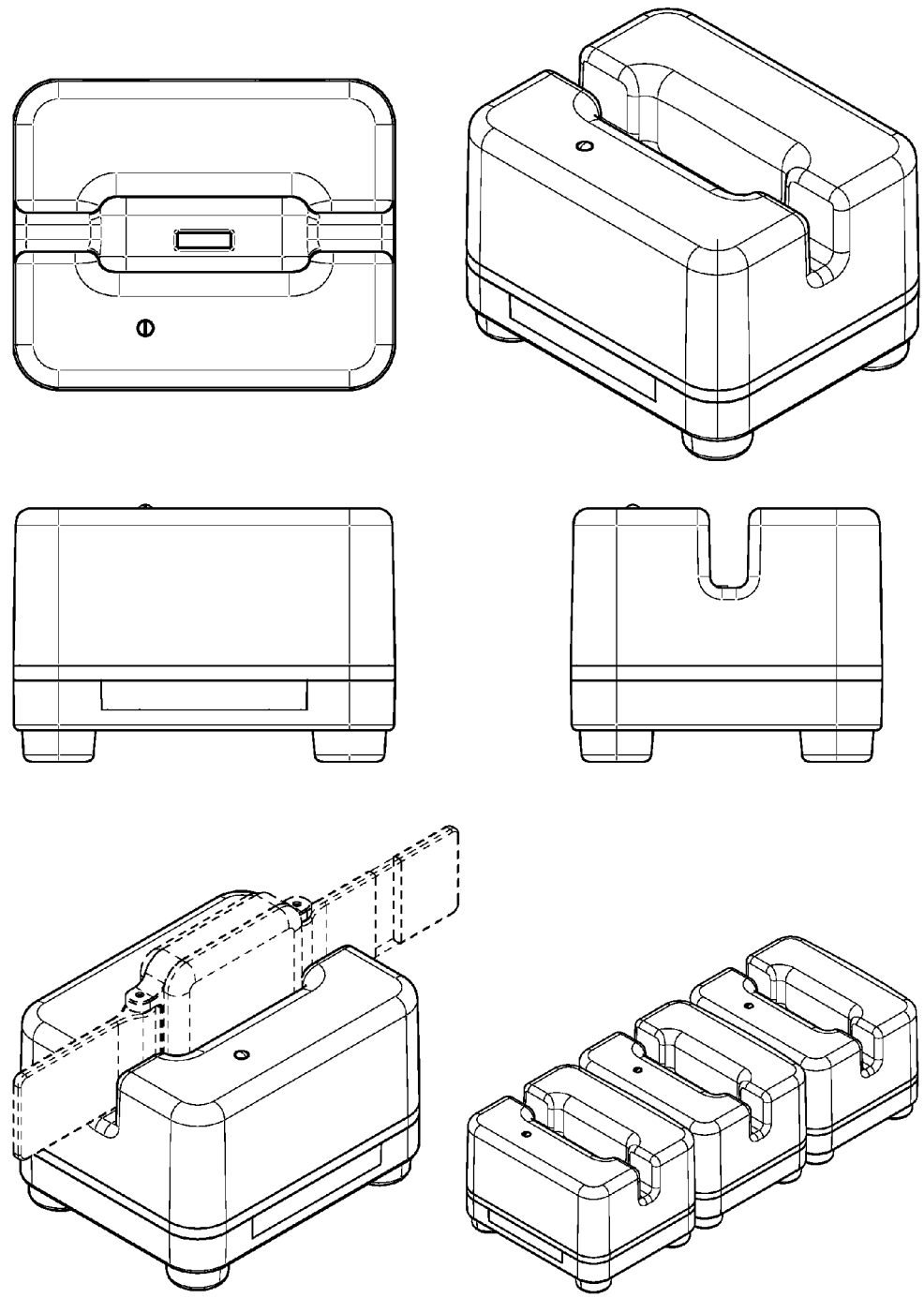
FIG. 10 illustrates an embodiment of the docking station and a connected docking station for simultaneously charging multiple movement monitors.

FIG. 7 illustrates a particular embodiment of the movement monitor, the docking station, and the docking mechanism. FIG. 8 illustrates a second embodiment of the movement monitor, the docking station, and the docking mechanism, this embodiment particularly adapted to the wearable a wrist watch. FIG. 10 illustrates an embodiment of the docking station and a connected docking station for simultaneously charging multiple movement monitors.

B.9. Clinical Data Management and Processing Module

Once the data is uploaded to the server 104 including a clinical data management tool, the server 104 runs automatic statistical signal processing methods 106 to analyze the data and compute the results needed for the application. According to one embodiment, the system provides data for three applications: 1) human movement research, 2) movement disorders studies and clinical trials, and 3) clinical care. The system provides a simple means for researchers to conduct studies in human movement with wearable sensors 100. Study participants have an easy means of handling the devices by simply docking them when not in use. Researchers have easy, secure, and protected access to their raw sensor data through the server 104. The system also provides full support for research studies and clinical trials in movement disorders such as Parkinson's disease and essential tremor. It permits researchers to easily upload other types of data such as clinical rating scale scores, participant information, and other types of device data integrated into a secure database, and provides a means for sharing the data. Different views and controlled access permit study coordinators, research sponsors, statisticians, algorithm developers, and investigators to easily monitor the progress of studies and results. The system also provides the ability to do sequential analysis for continuous monitoring of clinical studies. According to one embodiment, the system has strict, secure, and encrypted access to any protected health information that is stored in the server. The system also supports clinical monitoring of individual patients to determine their response to therapy. This is especially helpful for movement disorders such as advanced Parkinson's in which the degree of motor impairment fluctuates continuously throughout the day. As with clinical studies and trials, the server provides secure, encrypted access to patient records for authenticated care providers as well as patients themselves.

According to one embodiment, the algorithms 106 process the raw device data and extract the metrics of interest. These algorithms are insensitive to normal voluntary activities, but provide sensitive measures of the motor impairments of interest. In Parkinson's disease this may include tremor, gait, balance, dyskinesia, bradykinesia, rigidity, and overall motor state.

Certain specific details are set forth in the above description and figures to provide a thorough understanding of various embodiments disclosed. Certain well-known details often associated with computing, firmware, and software technology are not set forth in the following disclosure to avoid unnecessarily obscuring the various disclosed embodiments. Further, those of ordinary skill in the relevant art will understand that they can practice other embodiments without one or more of the details described below. Aspects of the disclosed embodiments may be implemented in the general context of computer-executable instructions, such as program modules, being executed by a computer, computer server, or device containing a processor. Generally, program modules include routines, programs, objects, components, data structures, etc. that perform particular tasks or implement particular abstract data types. Aspects of the disclosed embodiments may also be practiced in distributed computing environments where tasks are performed by remote processing devices that are linked through a communications network. In a distributed computing environment, program modules may be located in both local and remote storage media including memory storage devices. Those skilled in the art will appreciate that, given the description of the modules comprising the disclosed embodiments provided in this specification, it is a routine matter to provide working systems which will work on a variety of known and commonly available technologies capable of incorporating the features described herein.

While particular embodiments have been described, it is understood that, after learning the teachings contained in this disclosure, modifications and generalizations will be apparent to those skilled in the art without departing from the spirit of the disclosed embodiments. It is noted that the foregoing embodiments and examples have been provided merely for the purpose of explanation and are in no way to be construed as limiting. While the system has been described with reference to various embodiments, it is understood that the words that have been used herein are words of description and illustration, rather than words of limitation. Further, although the system has been described herein with reference to particular means, materials and embodiments, the actual embodiments are not intended to be limited to the particulars disclosed herein; rather, the system extends to all functionally equivalent structures, methods and uses, such as are within the scope of the appended claims. Those skilled in the art, having the benefit of the teachings of this specification, may effect numerous modifications thereto and changes may be made without departing from the scope and spirit of the disclosed embodiments in its aspects.

The invention claimed is:

1. A wearable movement monitoring apparatus comprising:
   (a) a kinematics sensor module with a resolution of 14 bits or more comprising an accelerometer, a gyroscope, a magnetometer, or combinations thereof, and said kinematics sensor configured to acquire more than 20 samples per second; and
   (b) a bidirectional wireless communication module configured to wirelessly synchronize the sampling time instances of said kinematics sensor module with the sampling time instances of at least a second wearable movement monitoring apparatus using a wireless synchronization scheme/protocol, said bidirectional wireless communication module including a chip antenna, a printed circuit board antenna, or a patch antenna.

2. The movement monitoring apparatus of claim 1, wherein said wireless synchronization scheme is a master synchronization scheme or a mesh synchronization scheme.

3. The movement monitoring apparatus of claim 2, further comprising a robust wireless data transfer data controller.

4. The movement monitoring apparatus of claim 3, wherein said mesh synchronization scheme includes a statistical model of a network time and of said movement monitor apparatus relative to said network time.

5. The wearable movement monitoring apparatus of claim 4, wherein said statistical model of the network time is a distributed statistical clock model.

6. The wearable movement monitoring apparatus of claim 5, wherein said mesh synchronization scheme is based on a flooding time synchronization protocol.

7. The wearable movement monitoring apparatus of claim 6, wherein said flooding time synchronization scheme is modified to enable said movement monitoring apparatus to broadcast its estimated clock model parameters and enable a root node to estimate its own parameters.

8. The wearable movement monitoring apparatus of claim 3, wherein said robust wireless data transfer data controller stores data packets locally whenever a transmission error is detected, and re-transmits said data packets at a later point in time, whereby no data packets are lost during wireless data transfers.

9. The wearable movement monitoring apparatus of claim 2, wherein said mesh synchronization scheme 1) avoids a master time source, 2) configures each movement monitoring apparatus in a wireless network to send a synchronization packet during a prescribed time slot, 3) compares a local clock against one or more clocks of other movement monitors in said wireless network, and 4) creates a distributed statistical clock model of said network time and of said local clock relative to said network time.

10. The wearable movement monitoring apparatus of claim 1, wherein said bidirectional wireless communication module comprises a low power bidirectional transceiver configured for transmitting and receiving wireless communications.

11. The wearable movement monitoring apparatus of claim 1, wherein said kinematics sensor module comprises a low power three-axis low-noise accelerometer and a low power three-axis low-noise gyroscope.

12. The wearable movement monitoring apparatus of claim 1, wherein said kinematics sensor module further includes a temperature sensor.

13. The wearable movement monitoring apparatus of claim 1, further comprising a data storage module including an onboard solid state local storage medium configured for multi-day local storage of movement monitoring data at sampling frequencies greater than 20 samples per second.

14. The wearable movement monitoring apparatus of claim 3, wherein said robust data transfer controller is configured to send movement monitoring data to a low power radio and store said movement monitoring data locally whenever a failed transmission is detected.

15. The wearable movement monitoring apparatus of claim 14, wherein said robust data transfer controller is further configured to 1) store movement monitoring data to said onboard solid state local storage medium while sensing the state of a communication channel, 2) shut off said low power radio to save power while continuing to poll said communication channel, and 3) transmit said movement monitoring data when said communication channel becomes available.

16. The wearable movement monitoring apparatus of claim 3, wherein said robust data transfer controller is configurable for 1) optimizing power, 2) optimizing communication bandwidth, or 3) optimizing robustness to lost data packets.

17. The wearable movement monitoring apparatus of claim 11, wherein said kinematics sensor module further comprises a low power three-axis low-noise magnetometer.

18. The wearable movement monitoring apparatus of claim 1, wherein said movement monitoring apparatus is a lightweight device further comprising a power module including a Lithium Ion Polymer battery.

* * * * *